(12) United States Patent
Kember et al.

(10) Patent No.: US 11,014,894 B2
(45) Date of Patent: May 25, 2021

(54) PROCESS FOR THE PRODUCTION OF TETRAAMINOBIPHENOL MACROCYCLIC LIGANDS; AND NOVEL TETRAAMINOBIPHENOL MACROCYCLIC LIGANDS

(71) Applicant: Econic Technologies Ltd., Macclesfield (GB)

(72) Inventors: Michael Kember, Macclesfield (GB); Anthony Chartoire, Macclesfield (GB); Anthea Blackburn, Macclesfield (GB); Samuel Drane, Macclesfield (GB)

(73) Assignee: ECONIC TECHNOLOGIES LIMITED, Macclesfield (GB)

( * ) Notice: Subject to any disclaimer, the term of this patent is extended or adjusted under 35 U.S.C. 154(b) by 0 days.

(21) Appl. No.: 16/487,939

(22) PCT Filed: Mar. 2, 2018

(86) PCT No.: PCT/GB2018/050547
§ 371 (c)(1),
(2) Date: Aug. 22, 2019

(87) PCT Pub. No.: WO2018/158592
PCT Pub. Date: Sep. 7, 2018

(65) Prior Publication Data
US 2019/0382357 A1     Dec. 19, 2019

(30) Foreign Application Priority Data
Mar. 2, 2017 (GB) .................................. 1703384

(51) Int. Cl.
C07D 257/10 (2006.01)
C07D 487/06 (2006.01)

(52) U.S. Cl.
CPC ......... *C07D 257/10* (2013.01); *C07D 487/06* (2013.01)

(58) Field of Classification Search
None
See application file for complete search history.

(56) References Cited

U.S. PATENT DOCUMENTS

2017/0204221 A1  7/2017  Keyworth et al.
2017/0210848 A1  7/2017  Chapman et al.

FOREIGN PATENT DOCUMENTS

WO  2016012785 A1  1/2016
WO  2017037441 A1  3/2017

OTHER PUBLICATIONS

Parvari et al, Chemical Communications (Cambridge, United Kingdom), 50(19), pp. 2494-2497 (Year: 2014).*
International Search Report for International application No. PCT/GB2018/050547; dated Apr. 20, 2018; 5 pages.
Eiji Asato et al., "New Pyridine-modified Macrocycle and Its Ability to Encapsulate Four Divalent Metal Ions [Nickel (II), Manganese (II), and Zinc (II)] into the Ring"; dated Mar. 15, 1999; Published in the Chemistry Letters vol. 28, No. 7, Jul. 1, 1999; pp. 647-648.
Victor N. Pastushok et al., "Mannich Reaction as a Key Strategy for the Synthesis of Benzoazacrown Ethers and Benzocrown Ethers and Benzocryptands", published in Journal of Organic Chemistry,vol. 61, No. 20, Jan. 1, 1996, pp. 6888-6892.
Wei-Jie Gong et al., "An unprecedented octahedral {Cd30} nanocage supported by twelve pendant-armed tetraacetate macrocyclic ligands", pubished in Dalton Transaction: The International Journal for Inorganic, Organometallic and Bioinogranic Chemistry, vol. 42, No. 10, Jan. 1, 2013, p. 3304-3307.
Wei-Jie Gong et al., "Supplementary Material (ESI) for Dalton Transactions an unprecedented octahedral {Cd30} nanocage supported by twelve pendant-armed tetraacetate macrocyclic ligands", Jan. 1, 2013, 10 pages.
Yuji Miyazato et al., "Synthesis and Characterization of a Di--oxalato Tertracopper (II) Complex with Teranucleating Macrocyclic Ligand", published in Bullentin of the Chemical Society of Japan, vol. 89, No. 4, Apr. 15, 2016, pp. 430-436.
Yuji Miyazato et al., "Synthesis and Characterization of a Di-oxalato Tertracopper (II) Complex with Having a [Cu4 (μ4—O)] Framework Stabilized by the Tetranueleating Macrocyclic Ligand.", published in Bullentin of the Chemical Society of Japan, vol. 85, No. 8, Aug. 3, 2012, pp. 8895-8901.
Search Report for application No. GB17403384.6; dated Dec. 12, 2017; 3 pages.
Chen et al., "A series of tetranuclear-cluster containing complexes based on pendent-arm macrocyclic ligand and different carboxylates: syntheses, structures, photoluminescence, and magnetic properties", CrystEngComm, 2013,15, pp. 5168-5178.
Hodgkin, "Linear aminophenol polymers using the mannich reaction," Polymer Science: Part A: Polymer Chemistry Edition, vol. 24, Abstract provided 4 pages; first published Nov. 1986.
Lee et al, Facile Synthesis of Alkyl Phenyl Ethers Using Cesium Carbonate, Synthetic Communications, 25(9), 1367-1370 (1995); Abstract provided 4 pages.
International Preliminary Report on Patentability for application No. PCT/GB2018/050547; dated Sep. 3, 2019; 5 pages.

* cited by examiner

*Primary Examiner* — Zinna Northington Davis
(74) *Attorney, Agent, or Firm* — Shumaker, Loop & Kendrick, LLP

(57) ABSTRACT

A process for preparing a tetra-substituted aminobiphenol macrocyclic ligand having the structure (I), comprising the step of treating a precursor compound having the structure (II) with a compound having the structure R6-L where L represents a leaving group (hereinafter compound (III)) in the presence of a base.

26 Claims, No Drawings

PROCESS FOR THE PRODUCTION OF TETRAAMINOBIPHENOL MACROCYCLIC LIGANDS; AND NOVEL TETRAAMINOBIPHENOL MACROCYCLIC LIGANDS

CROSS REFERENCE TO RELATED PATENT APPLICATIONS

This application claims the benefit of and priority to PCT/GB2018/050547 filed Mar. 2, 2018 which claims the benefit of and priority to Great Britain Application No. 1703384.6 filed on Mar. 2, 2017.

TECHNICAL FIELD AND BACKGROUND OF THE INVENTION

The present invention relates to an improved process for the production of tetraaminobiphenol macrocyclic ligands, in particular, tetraaminobiphenol macrocyclic ligands for use in the production of bimetallic catalysts employed in copolymerization reactions.

The invention relates in particular to an improved process for the production of tetraaminobiphenol macrocyclic ligands in which each of the amino moieties of the macrocyclic ligand is substituted, for example alkylated or allylated.

The invention further relates to novel tetraaminobiphenol macrocyclic ligands.

It is disclosed in Hodgkin, Polymer Science: Part A: Polymer Chemistry Edition, Vol. 24, 3117-3127 (1986), that a Mannich reaction between p-cresol, and N,N'-dimethylethylenediamine and formaldehyde yielded a tetramethylaminobiphenol macrocyclic ligand. The process is as shown in outline below.

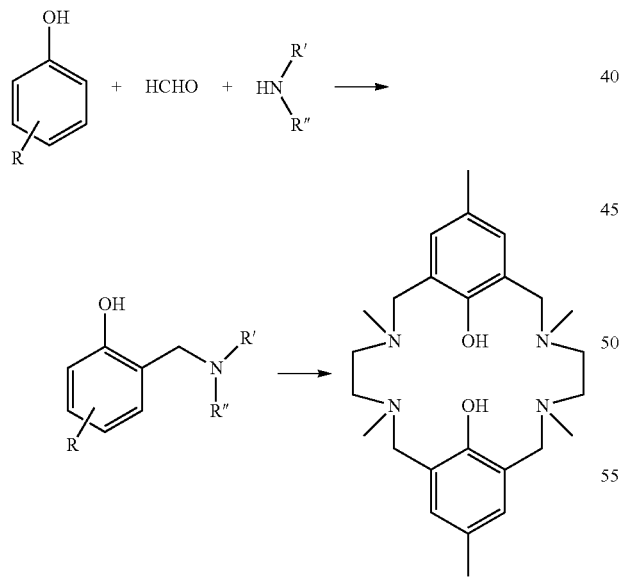

In this method there is no alkylation step carried out on the macrocyclic ligand and therefore no risk of alkylating the phenol moieties. However, the process has disadvantages. The macrocycle is formed in low yields as a by-product to the linear polymeric products that were the target of Hodgkin et al. There is no indication that any other macrocyclic product could be made; but if this method were possible for different substituents of the amine groups it would be necessary to run a new Mannich reaction for each macrocyclic ligand.

Direct alkylation of a tetraaminobiphenol macrocyclic ligand is described in Chen et al., CrystEngComm, 2013, 15, 5168-5178. In this reference it is stated that a tetraaminobiphenol macrocyclic ligand (3 mmol) was reacted with ethylchloroacetate (6 mmol) and potassium carbonate (24 mmol) in dimethylformamide under reflux for 20 hours. Following filtration and evaporation the residue was hydrolysed with sodium hydroxide to give the desired tetracarboxylic acid ligand. The reaction scheme is shown in outline below:

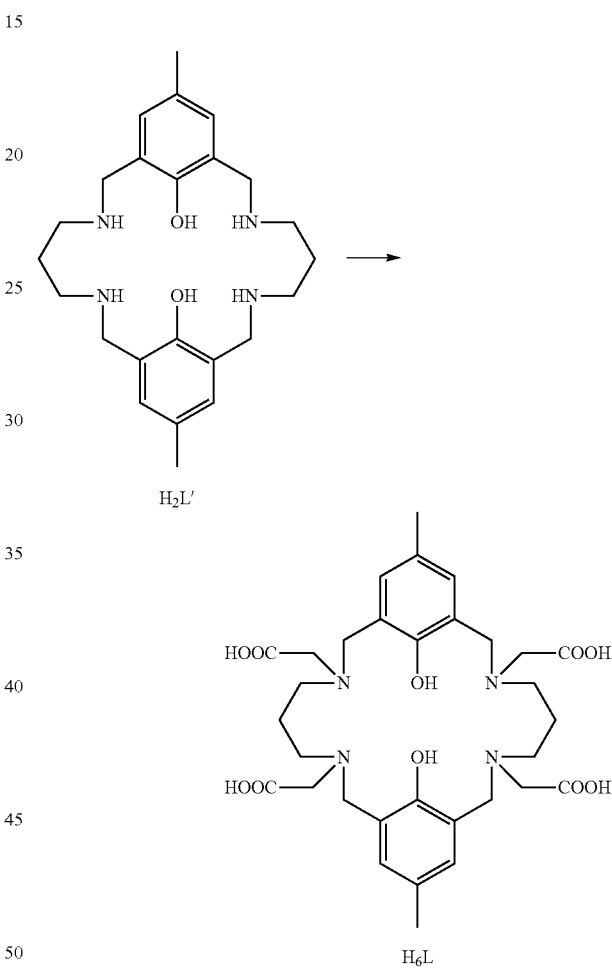

It is stated in the Chen reference that the tetracarboxyaminobiphenol ligand $H_6L$ was obtained in 65% yield. However this yield is not possible: only two equivalents of ethylchloroacetate were used, per one equivalent of the tetraaminobiphenol macrocyclic ligand $H_2L'$. It will be appreciated that the tetraaminobiphenol macrocyclic ligand of interest in the Chen reference has four N-sites and two phenolic moieties, all of which are potential sites for reaction. Thus the theoretical maximum of the yield of the tetracarboxyaminobiphenol ligand is 50%; and this would assume no other products; for example no mono-carboxy ligand, no di-carboxyaminobiphenol ligand, no tri-carboxyaminobiphenol ligand, and no alkylated phenol ligands of any sort. It may be noted here that alkylation of phenol moieties under basic conditions is commonplace and is described in chemistry textbook. One literature example (from many) is *Facile Synthesis of Alkyl Phenyl Ethers Using Cesium Carbonate*, Lee et al, Synthetic Communications, 25(9), 13671370 (1995) which describes a "highly efficient" alkylation method of phenols using alkyl halides/cesium carbonate/acetonitrile. For Chen to choose to use such a low amount of the alkylating agent—two mole equivalents when the target product has 4 moles of the carboxylate substituent—may indicate a desire to avoid competing reactions, such as alkylation of the phenol groups.

BRIEF SUMMARY OF THE INVENTION

In accordance with a first aspect of the present invention there is provided a process for preparing a tetra-substituted aminobiphenol macrocyclic ligand having the structure (I), comprising the step of treating a precursor compound having the structure (II) with a compound having the structure $R_6$-L where L represents a leaving group (hereinafter compound (III)) in the presence of a base;

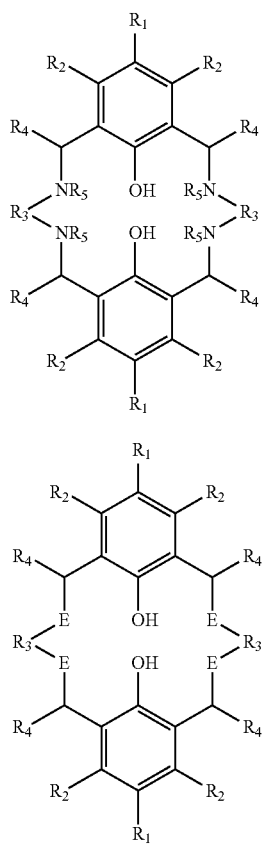

wherein $R_1$ and $R_2$ are independently selected from hydrogen, halide, a nitro group, a nitrile group, an imine group, —$NCR_{13}R_{14}$, an amine, an ether group —$OR_{15}$ or —$R_{16}OR_{17}$, an ester group —$OC(O)R_{10}$ or —$C(O)OR_{10}$, an amido group —$NR_9C(O)R_9$ or —$C(O)$—$NR_9(R_9)$, —COOH, —$C(O)R_{15}$, —$OP(O)(OR_{18})(OR_{19})$, —$P(O)R_{20}R_{21}$, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

$R_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, in each case optionally interrupted by aryl, heteroaryl, alicyclic or heteroalicyclic;

$R_4$ is independently selected from hydrogen, or optionally substituted aliphatic, heteroaliphatic, alicyclic, heteroalicyclic, aryl, heteroaryl, alkylheteroaryl or alkylaryl;

$R_5$ is independently selected from hydrogen, optionally substituted aliphatic, heteroaliphatic, alicyclic, alkanoate, arylate, carboxyl, heteroalicyclic, aryl, heteroaryl, alkylheteroaryl or alkylaryl, or two R5 species may together be selected from optionally substituted alkylene, alkenylene or alkynylene, bonded to two different N groups of the compound of structure (II), with the proviso that at least one of the species $R_5$ is hydrogen;

and E is independently selected from $NR_5$ and $NR_6$, with the proviso that at least one of the species E is $NR_6$;

wherein $R_6$ is independently selected from optionally substituted aliphatic, alicyclic, heteroalicyclic, aryl, heteroaryl, ether, polyether, or optionally substituted alkylaryl or alkylheteroaryl; and wherein $R_9$, $R_{10}$, $R_{13}$, $R_{14}$, $R_{18}$, $R_{19}$, $R_{20}$ and $R_{21}$ are independently selected from hydrogen or an optionally substituted aliphatic, heteroaliphatic, alicyclic, heteroalicyclic, aryl or heteroaryl group and $R_{15}$, $R_{16}$ and $R_{17}$ are independently selected from an optionally substituted aliphatic, heteroaliphatic, alicyclic, heteroalicyclic, aryl or heteroaryl group;

wherein the molar ratio of compound of structure (III) to the number of NH sites in the compound of structure (II) is at least 0.6.

Preferably the molar ratio of the compound having the structure (III) to species $R_5$ which are hydrogen in the compound having the macrocycle (II)—i.e. the number of NH sites in the macrocycle—is at least 0.8.

Preferably the molar ratio of the compound having the structure (III) to the number of NH sites in the macrocycle (II) is at least 1.

In especially preferred embodiments the molar ratio of the compound having the structure (III) to the number of NH sites in the macrocycle (II) is at least 1.1.

In a preferred process of the present invention the molar ratio of the compound having the structure (III) to the number of NH sites in the macrocycle (II) is not greater than 2; preferably not greater than 1.6; preferably not greater than 1.4.

'The number of NH sites in the macrocycle (II)' may alternatively be referred to as 'the species $R_5$ which are hydrogen in compound (II)'.

In preferred embodiments the molar ratio of the compound of structure (III) to the compound of structure (II) is at least 2.2, preferably at least 2.4.

One sub-group of compounds having the structure (IIa) shown below (and conforming to the more general structure (II)) has a single group $R_5$ which is hydrogen and the remaining three groups $R_5$ which are any of the groups mentioned above, but not hydrogen. In this subgroup the molar ratio of the compound having the structure (III) to the compound of structure (IIa) is at least 0.6, preferably at least 0.8, more preferably at least 1, and in especially preferred embodiments at least 1.1. In the sub-group of compounds having the structure (IIa) the molar ratio of the compound having the structure (III) to the compound of structure (IIa) is preferably not greater than 2; preferably not greater than 1.6; preferably not greater than 1.4.

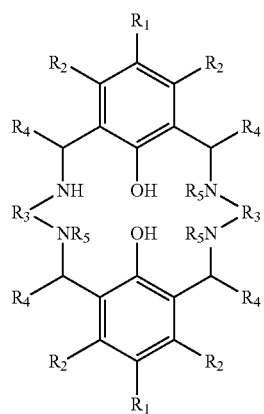

(IIa)

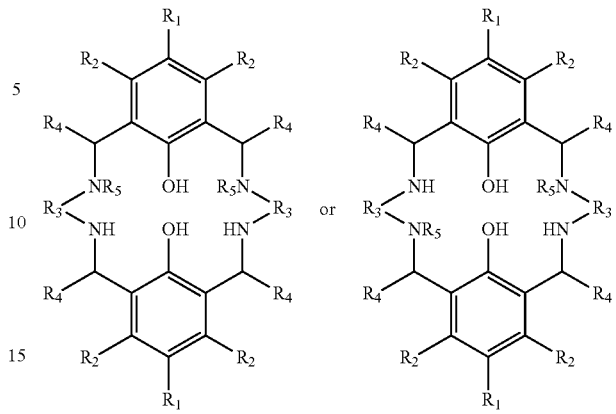

One sub-group of compounds having the structure (IIc) shown below (and conforming to the more general structure (II)) has three group $R_5$ which are hydrogen and the remaining single group $R_5$ which is any of the groups mentioned above, but not hydrogen. In this subgroup the molar ratio of the compound having the structure (III) to the compound of structure (IIc) is at least 1.8, preferably at least 2.4, more preferably at least 3, and in especially preferred embodiments at least 3.3. In the sub-group of compounds having the structure (IIc) the molar ratio of the compound having the structure (III) to the compound of structure (IIc) is preferably not greater than 6; preferably not greater than 4.8; preferably not greater than 4.2.

One sub-group of compounds having the structure (IIb) shown below (and conforming to the more general structure (II)) has two groups $R_5$ which are hydrogen and the remaining two groups $R_5$ which are any of the groups mentioned above, but not hydrogen. In this subgroup the molar ratio of the compound having the structure (III) to the compound of structure (IIb) is at least 1.2, preferably at least 1.6, more preferably at least 2, and in especially preferred embodiments at least 2.2. In the sub-group of compounds having the structure (IIb) the molar ratio of the compound having the structure (III) to the compound of structure (IIb) is preferably not greater than 4; preferably not greater than 3.2; preferably not greater than 2.8.

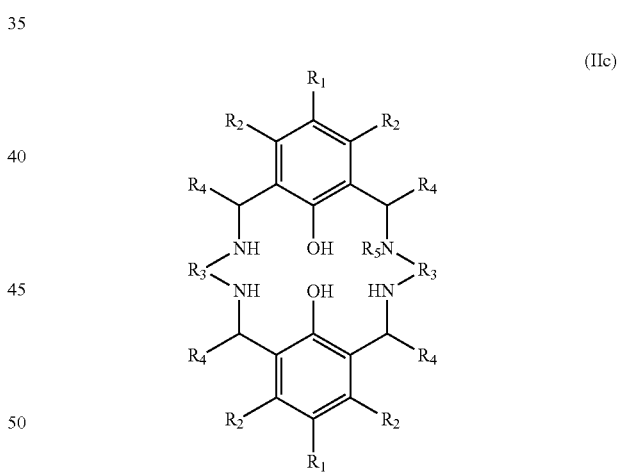

(IIc)

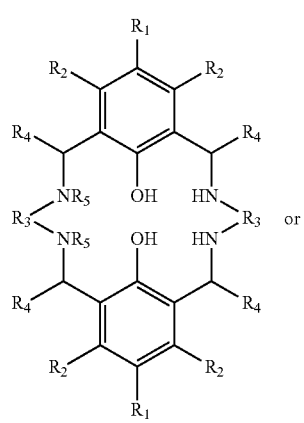

(IIb)

One preferred sub-group of compounds having the structure (IId) shown below and (conforming to the more general structure (II)) has all four groups $R_5$ which are hydrogen. In this subgroup the molar ratio of the compound having the structure (III) to the compound of structure (IId) is at least 2.4, preferably at least 3.2, preferably at least 3.6, more preferably at least 4, more preferably at least 4.2, and in especially preferred embodiments at least 4.4. In the sub-group of compounds having the structure (IId) the molar ratio of the compound having the structure (III) to the compound of structure (IId) is preferably not greater than 8; preferably not greater than 6.4; preferably not greater than 5.6.

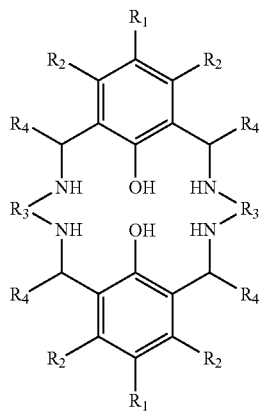

(IId)

The process of the present invention uses a significantly higher molar ratio of compound (III) to species $R_5$ which are hydrogen in compound (II), compared with the prior art of Chen, mentioned above. In Chen's publication the molar ratio of the chloroethylacetate to the four alkylatable NH groups on the ligand $H_2L'$ is 0.5.

Surprisingly, the present inventors have found that very high yields of the target substituted aminobiphenol ligands of formula I can be obtained, despite the presence of the phenol sites at which reaction might be expected, and use of a high molar ratio of reactant (III). To the inventors' surprise, the use of such a high mole ratio of the reactant (III) does not appear to promote competing reactions at the phenolic —OH sites. Rather, it produces the compound of formula (I) in high yield and at high selectivity.

Each of the occurrences of the groups $R_1$ and $R_2$ may be the same or different. Preferably, $R_1$ and $R_2$ are independently selected from hydrogen, halide, amino, nitro, sulfoxide, sulfonyl, sulfinate, silyl, silyl ether and an optionally substituted alkyl, alkenyl, aryl, heteroaryl, heteroalicyclic, alkoxy, aryloxy or alkylthio.

Preferably, each occurrence of $R_2$ is the same, and is hydrogen or alkyl, for example methyl. Preferably $R_2$ is hydrogen.

Even more preferably, $R_2$ is alkyl or, especially, hydrogen, and $R_1$ is independently selected from hydrogen, halide, amino, nitro, sulfoxide, sulfonyl, sulfinate, silyl, silyl ether and optionally substituted alkyl, alkenyl, aryl, heteroaryl, heteroalicyclic, alkoxy, aryloxy, alkylthio orarylthio, such as hydrogen, $C_{1-6}$alkyl (e.g. haloalkyl), alkoxy, aryl, halide, nitro, sulfonyl, silyl and alkylthio, for example t-butyl, n-butyl, i-propyl, methyl, piperidinyl, methoxy, hexyl methyl ether, —$SCH_3$, —$S(C_6H_5)$, H, nitro, trimethylsilyl, methylsulfonyl (—$SO_2CH_3$), triethylsilyl, halogen or phenyl.

Each occurrence of $R_1$ can be the same or different, and $R_1$ and $R_2$ can be the same or different. Preferably each occurrence of $R_1$ is the same. Preferably each occurrence of $R_2$ is the same. When $R_1$ and $R_2$ are the same, preferably each occurrence of $R_1$ and $R_2$ is hydrogen or methyl. Preferably, each occurrence of $R_1$ is the same, and each occurrence of $R_2$ is the same, and $R_1$ is different to $R_2$.

Preferably both occurrences of $R_1$ are the same, and are selected from hydrogen, halide, amino, nitro, sulfoxide, sulfonyl, sulfinate, silyl, silyl ether and an optionally substituted alkyl, alkenyl, aryl, heteroaryl, heteroalicyclic, alkoxy, aryloxy, or alkylthio. More preferably both occurrences of $R_1$ are the same, and are selected from halide, sulfoxide, silyl, and an optionally substituted alkyl, heteroaryl or alkoxy. Still more preferably both occurrences of $R_1$ are the same, and are selected from H, alkyl, aryl, alkoxy, trialkylsilyl such as triethylsilyl, or halide. More preferably still both occurrences of $R_1$ are the same, and are selected from H, alkyl, phenyl, halide or trialkylsilyl. Most preferably, both occurrences of $R_1$ are the same, and are selected from H, methyl, ethyl, n-propyl, i-propyl n-butyl, t-butyl, t-amyl, t-octyl, methylthio, methoxy and triethylsilyl.

It will be appreciated that the group $R_3$ can be the divalent alkylene, alkenylene, alkynylene, heteroalkylene, heteroalkenylene or heteroalkynylene group which may optionally be interrupted by an aryl, heteroaryl, alicyclic or heteroalicyclic group, or may be a divalent arylene or cycloalkylene group which acts as a bridging group between two nitrogen centres in the macrocycle of formula (I). Thus, where $R_3$ is an alkylene group, such as 2,2-dimethylpropane-1,3-diyl, the $R_3$ group has the structure —$CH_2$—$C(CH_3)_2$—$CH_2$—. The definitions of the alkyl, aryl, cycloalkyl etc groups set out herein therefore also relate respectively to the divalent alkylene, arylene, cycloalkylene etc groups set out for $R_3$, and may also be optionally substituted. Exemplary options for $R_3$ include ethane-1,2-diyl, 2,2-fluoropropane-1,3-diyl, 2,2-dimethylpropane-1,3-diyl, propane-1,3-diyl, butane-1,4-diyl, phenylene, cyclohexane-1,4-diyl, cyclohexane-1,2-diyl or biphenylene. When $R_3$ is cyclohexane-1,4-diyl or cyclohexane-1,2-diyl, it can be the racemic, RR- or SS-forms.

$R_3$ can be independently selected from substituted or unsubstituted alkylene, alkenylene, alkynylene, heteroalkylene, heteroalkenylene or heteroalkynylene, arylene or cycloalkylene. Preferably, $R_3$ is selected from substituted or unsubstituted alkylene, cycloalkylene, alkenylene, heteroalkylene and arylene. More preferably, $R_3$ is selected from —$CH_2C(CH_3)_2CH_2$—, —$CH_2CH_2CH_2$—, —$CH_2CH(CH_3)CH_2$—, —$CH_2C(CH_2C_6H_5)_2CH_2$—, —$(C_6H_4)$—, —$CH_2CH_2$—, —$CH_2$—$CH_2CH_2CH_2$—, —$CH_2CH_2N(CH_3)CH_2CH_2$—, —$(C_6H_{10})$— or —$CH_2CH_2CH(C_2H_5)$—. Still more preferably $R_3$ is selected from —$CH_2C(CH_3)_2CH_2$—, —$CH_2CH_2$—, —$CH_2CH_2CH_2$, —$CH_2CH(CH_3)CH_2$—, —$CH_2C(CH_2C6H_5)_2CH_2$—, —$CH_2CH_2CH(C_2H_5)$—, —$CH_2CH_2CH_2CH_2$—. More preferably still, $R_3$ is selected from —$CH_2C(CH_3)_2CH_2$—, $CH_2CH_2CH_2$—, —$CH_2CH(CH_3)CH_2$— and —$CH_2C(C_2H_5)_2CH_2$—.

$R_3$ can be independently selected from substituted or unsubstituted alkylenes and substituted or unsubstituted arylenes, preferably substituted or unsubstituted propylenes, such as propane-1,3-diyl and 2,2-dimethylpropane-1,3-diyl, and substituted or unsubstituted phenylene or biphenylene. Preferably both occurrences of $R_3$ are the same. Even more preferably $R_3$ is a substituted propane-1,3-diyl, such as 2,2-di(alkyl)propane-1,3-diyl, especially 2,2-dimethylpropane-1,3-diyl.

Preferably, each $R_4$ is independently selected from hydrogen, and optionally substituted aliphatic or aryl. More preferably, each $R_4$ is independently selected from hydrogen, and optionally substituted alkyl or aryl. Even more preferably, each $R_4$ is the same, and is selected from hydrogen, and optionally substituted alkyl or aryl. Exemplary $R_4$ groups include hydrogen, methyl, ethyl, n-propyl, n-butyl, phenyl and trifluoromethyl, preferably hydrogen, methyl or trifluoromethyl. Even more preferably, each $R_4$ is hydrogen.

In preferred combinations of the $R_4$ group and $R_1$ group, $R_1$ is selected from H, methyl, ethyl, n-propyl, n-butyl, t-butyl, t-octyl, Cl, Br, F, nitro, trimethylsilyl, triethylsilyl, methoxy or methylthio and $R_4$ is selected from H, methyl, ethyl, n-propyl, phenyl, trifluoromethyl.

Preferably R$_5$ is independently selected from hydrogen, optionally substituted aliphatic, heteroaliphatic, alicyclic, alkanoate, arylate, carboxyl, heteroalicyclic, aryl, heteroaryl, alkylheteroaryl or alkylaryl; or two R5 groups may together be an optionally substituted alkylene group, for example a C(1-10alkylene) group optionally substituted by an optionally substituted aryl group. At least one species R$_5$ is hydrogen. In embodiments of the invention one, two, three or four species R$_5$ may be hydrogen, as shown in structures (IIa)-(IId) above. Species NR$_5$ which are NH provide a site or sites for reaction of the compound of structure (III) and introduction of the species R$_6$. Thus an NH species in the compound of structure (II) can provide the site for an NR$_6$ species in the compound of structure (I).

Preferably R$_5$ is independently selected from hydrogen, optionally substituted alkyl which is optionally interrupted by at least one N atom, or by at least one O atom, or by at least one S atom, optionally substituted alkylthio, alkylaryl, alkylheteroaryl, alkenyl, alkynyl, heteroalkenyl, heteroalkynyl, aryl, heteroaryl, alicyclic, heteroalicyclic, sulfonate, alkanoate (—C(O)—OR$_{10}$), carbonyl (—C(O)—R$_{10}$), ether or, polyether, arylate, or carboxyl. More preferred R$_5$ species include optionally substituted groups selected from alkyl (such as methyl, ethyl, propyl, butyl), alkylaryl, alkylheteroaryl (such as benzyl, substituted benzyl or methyl pyridine), alkenyl (such as allyl), alkynyl (such as propargyl), sulfonate (such as tosylate), alkanoate (such as —C(O)—O-t-butyl (BOC), —C(O)—O-benzyl, —C(O)—O-9-fluorenylmethyl (FMOC)), and optionally substituted aryl-C(O)OR$_{10}$, alkylaryl-C(O)OR$_{10}$, alkyl-C(O)—OR$_{10}$ (such as —CH$_2$—C(O)—OMe, —CH$_2$CH$_2$—C(O)—OMe) or alkyl-C≡N (such as —CH$_2$CH$_2$—C≡N). Most preferred species R$_5$ include methyl, ethyl, propyl (preferably n-propyl), butyl (preferably n-butyl), allyl, propargyl, benzyl, 4-nitrobenzyl, —CH$_2$CH$_2$—C(O)—OR$_{10}$, —CH$_2$CH$_2$—C≡N. or —C(1-4)alkylC(O)O—, for example, acetate or propanoate, or optionally substituted alkylarylC(O)O— or arylC(O)O—, for example benzoate which is unsubstituted or ring-substituted by 1, 2 or 3 C(1-4)alkyl groups. It will be appreciated that some of the groups defined above will be associated with a cation. The cation will typically be a sodium, lithium or ammonium cation.

When there is a plurality of groups R$_5$ which are not hydrogen, such groups may be identical or they may all differ from each other.

In some embodiments two R$_5$ species are together selected from methylene —CH$_2$—, ethylene —CH$_2$—CH$_2$—, propylene —CH$_2$—CH$_2$—CH$_2$— or phenylmethylene —CH(Ph)-, bonded to two different N groups of the compound of structure (II).

Preferably each R$_6$ is independently selected from optionally substituted aliphatic, alicyclic, heteroalicyclic, aryl, heteroaryl, ether, polyether, or optionally substituted alkylaryl or alkylheteroaryl. More preferably, each R$_6$ is independently selected from optionally substituted alkyl (such as methyl, ethyl, propyl, butyl), alicyclic (such as cyclohexane), alkenyl (such as allyl), alkynyl (such as propargyl) or alkylaryl (such as benzyl, substituted benzyl, methylpyridine, ether (such as methoxymethyl), polyether (such as polyethylene glycol (PEG), polypropylene glycol (PPG), Preferred R$_6$ groups include C(1-10)alkyl, preferably C(1-6)alkyl, more preferably C(1-4)alkyl, most preferably methyl, ethyl, n-propyl, n-butyl; or allyl or propargyl or benzyl.

In preferred combinations of the R$_6$ group and R$_1$ group, R$_1$ is selected from H, methyl, ethyl, n-propyl, n-butyl, t-butyl, t-octyl, Cl, Br, F, nitro, trimethylsilyl, triethylsilyl, methoxy or methylthio and R$_6$ is selected from methyl, ethyl, n-propyl, n-butyl, allyl and benzyl.

When there is a plurality of groups R$_6$ such groups are preferably identical.

Preferably each R$_5$ group is different from each R$_6$ group.

The compound having the structure (III) introduces groups R$_6$ to provide the compound of formula (I). The leaving group L of the compound having the structure (III) is preferably selected from halogen, for example: chloro, bromo or iodo; or an ether group (for example when the compound R$_6$-L is a trialkyloxonium compound); or a tertiary amine (for example when the compound R$_6$-L is a quaternary ammonium salt, for example a tetraalkyl ammonium salt; or a sulfonate group of formula —O—SO$_2$—R$_x$ where R$_x$ is selected from optionally substituted aliphatic or aryl or alkaryl; for example an alkyl sulfonate, aryl sulfonate, halo sulfonate or trifluoroalkyl sulfonate, for example tosylate, mesylate, triflate, fluorosulfonate, nosylate or brosylate; or a group of formula —O—SO$_2$—O—R$_y$, or —O—CO—O—R$_y$, where R$_y$ represents optionally substituted aliphatic or aryl or alkaryl, preferably an alkyl group, for example methyl and ethyl. Sulfonate compounds suitable for use in the present invention may be polymer-bound, for example on polystyrene. When the leaving group L is of formula —O—SO$_2$—O—R$_y$, or —O—CO—O—R$_y$, it is preferred that R$_6$ and R$_y$ are identical.

Preferably they are both C$_{(1-4)}$ alkyl groups, preferably both methyl or both ethyl.

A base for use in the process of the first aspect may be an inorganic base or an organic base. Preferred inorganic bases include metal compounds, for example of Group 1 and Group II metals. Preferred metal compounds are carbonates, hydrogen carbonates, alkanoates, hydroxides, silicates, phosphates and borates. Preferred cationic species thereof are Group 1 metals, most preferably sodium, potassium or cesium; Group II metals, preferably magnesium, calcium, strontium and barium; or ammonium. Preferred anionic species of the metal compounds are (C1-4) alkanoates (especially acetates), carbonates, and hydroxides. Preferred bases include sodium carbonate, potassium carbonate, cesium carbonate, magnesium carbonate, calcium carbonate, ammonium carbonate, sodium hydroxide, potassium hydroxide, magnesium hydroxide, calcium hydroxide, ammonium hydroxide, sodium (C1-10) alkanoates, preferably sodium (C1-4) alkanoates, especially sodium acetate, potassium alkanoates, preferably potassium (C1-4) alkanoates, especially potassium acetate, sodium metasilicate, potassium metasilicate, sodium borate, potassium borate, trisodium phosphate, disodium phosphate, monosodium phosphate, monopotassium phosphate, dipotassium phosphate and tripotassium phosphate. Especially preferred bases are sodium carbonate, potassium carbonate, sodium acetate, potassium acetate, mono-, di- or trisodium phosphate, mono-, di- or tripotassium phosphate, sodium hydroxide or potassium hydroxide.

Preferred organic bases include tertiary amine bases, suitably carrying groups selected from alkyl and alkylene. Preferably tertiary alkylamine bases have from 1 to 3 amine groups and C(1-10) alkyl or C(1-10) alkylene groups in place of all N-hydrogen species. Preferred tertiary alkylamine bases are of formula (C1-10alkyl)$_3$-N, especially triethylamine, tripropylamine, tributylamine, tri-isobutylamine or diisopropylethylamine. Preferred organic bases may further include trialkanolamine bases, especially triethanolamine.

A preferred base for use in the process of the invention has a pKb in the range from −2 to 14 when in an aqueous solution. It will be understood that the process of the present invention need not employ aqueous conditions and therefore that the pKb of the base does not represent any measurable pKb under the reaction conditions. Rather it is used a representation of the strength of the base and it is believed to provide a useful guide to bases which are suitable for use in the present invention. In preferred embodiments the pKb in the range at least 0 (zero) to less than 13.5. Preferably the base has a pKb of at least 0, preferably at least 0.5, preferably at least 1, more preferably at least 2, more preferably at least 3. Preferably it has a pKb of not greater than 13, preferably not greater than 12, more preferably not greater than 10.

The process of the present invention may take place in the presence of a solvent. However in embodiments of the invention the reactants described above, in particular the compound of structure (III) and/or the base, may function as the solvent, and no further solvent is employed.

When a solvent is employed (in addition to the reactant species), it may suitably be selected from substituted alkyl, optionally substituted alkanol (especially halogenated alkanol; suitable halogen atoms being chlorine, bromine and iodine), a cyclic ether, an aliphatic ether, a dialkylformamide, a ketone, an ester, a dialkyl sulfoxide, an alkyl nitrile optionally substituted aryl; or optionally substituted heteroaryl. Water may also be used in some embodiments. A single solvent or a mixture of solvents may be used.

Preferred solvents have up to 20 carbon atoms, preferably up to 12 carbon atoms, preferably up to 8 carbon atoms.

Preferred substituted alkyl groups include halo C(1-4) alkyl groups, preferably chloro (C1-4)alkyl groups, for example chloroform or dichloromethane.

Preferred alkanols and haloalkanols are methanol, ethanol, propanol, iso-propanol, iso-butanol, t-butyl alcohol, phenol, n-butanol and chlorocapryl alcohol. Especially preferred alkanols are methanol and ethanol. A particularly preferred alkanol is methanol.

Preferred cyclic ethers are optionally substituted cycloaliphatic compounds having from 5-8 ring atoms of which at least one ring atom is an oxygen atom. Preferred substituents are one or two C(1-4) alkyl groups.

Examples of suitable cyclic ethers include tetrahydrofuran, C(1-4)alkyl-substituted tetrahydrofurans, for example 2-methyl tetrahydrofuran, dioxane and dioxolane.

Preferred aliphatic ethers include simple ethers, for example alkylene interrupted by one or more oxygen atoms, being for example ethers of formula R—O—R where each R represents an alkyl group; or may be glycols, glycol ethers and dialkyl glycols. Preferred simple ethers have the formula C(1-6)alkyl-O—C(1-6)alkyl, for example dibutyl ether. Preferred glycols have the formula HO—C(1-6)alkyl-OH. Preferred glycol ethers have the formula C(1-6)alkyl-O—C(1-6)alkyl-OH. Preferred dialkyl glycols have the formula C(1-6)alkyl-O—C(1-6)alkyl-O—C(1-6)alkyl, for example dimethoxyethane.

Preferred alkyl nitriles are C(1-10)alkyl nitriles, preferably C(1-4)alkyl nitriles, for example acetonitrile.

Preferred dialkylformamides are di-C(1-10)alkyl formamides, preferably C(1-4)alkyl formamides, for example dimethyl formamide.

Preferred ketones are diC(1-10)alkyl ketones, preferably di(C(1-4)alkyl ketones, for example acetone.

Preferred esters are C(1-10)alkanoate esters, for example C(1-4)alkyl C(1-4) alkanoate esters, for example ethyl acetate.

Preferred dialkyl sulfoxides are di-C(1-10)alkyl sulfoxides, preferably di-C(1-4)alkyl sulfoxides, for example dimethyl sulfoxide.

Preferred optionally substituted aryl groups include benzene substituted by 1-3 (C(1-4) alkyl groups. Especially preferred alkylbenzene solvents include toluene, xylene and ethylbenzene.

A preferred optionally substituted heteroaryl group is pyridine.

Preferably, the process of the present invention is carried out at a temperature in the range 0 to 100° C., more preferably between 20 to 80° C. Some preferred embodiments are carried out at ambient temperature. Other preferred embodiments are carried out at the reflux temperature of the reaction system.

In a preferred process of the present invention the molar ratio of the base to the precursor compound having the structure (II) is at least 1; preferably at least 2; in some embodiments it is preferably at least 4; preferably at least 5.

In a preferred process of the present invention the molar ratio of the base to the precursor compound having the structure (II) is not greater than 7.5; preferably not greater than 6.

Preferably the molar ratio of the base to the number of NH sites in the compound of structure (II) is from 1 to 1.9, preferably from 1.1 to 1.8, and most preferably from 1.25 to 1.75.

Biphenol ligand precursors having the structure (II) used in the present invention and having four NH groups in the macrocyclic ring are described in publically available sources; for example in WO2016/012785 and in Chen et al., CrystEngComm, 2013, 15, 5168-5178, described above.

Biphenol ligand precursors having the structure (II) used in the present invention and having one, two or three NH groups in the macrocyclic ring (the other N atom having a substituent) may be prepared using protecting group chemistry in the absence of a base, as described in WO2016/012785. Alternative methods are described in Hodgkin, Polymer Science: Part A: Polymer Chemistry Edition, Vol. 24, 3117-3127 (1986), mentioned above.

Preferably the process of the present invention does not employ a protecting group protecting the phenol moieties. Surprisingly, it has been found that the process proceeds in high yield to the tetrasubstituted amino product of formula (I) even without such protection. In preferred embodiments of the invention yields of greater than 50% of the tetrasubstituted amino product of formula (I) are achieved, even without such protection. In preferred examples substantially higher yields have been obtained.

In the process of the invention the base may be dissolved in the reaction system. The base may be completely dissolved already at the start of the reaction. Alternatively the base may be heterogeneous, or may be partially dissolved, but able to accept protons as the reaction proceeds.

In accordance with a second aspect of the invention there is provided a compound of structure (Ie)

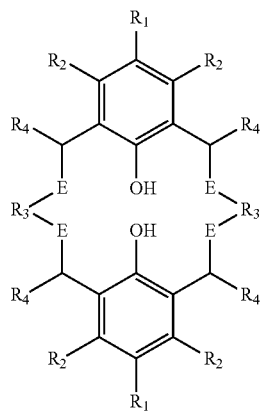

(Ie)

wherein $R_1$ and $R_2$ are independently selected from hydrogen, halide, a nitro group, a nitrile group, an imine group, —$NCR_{13}R_{14}$, an amine, an ether group —$OR_{15}$ or —$R_{16}OR_{17}$, an ester group —$OC(O)R_{10}$ or —$C(O)OR_{10}$, an amido group —$NR_9C(O)R_9$ or —$C(O)$—$NR_9(R_9)$, —COOH, —$C(O)R_{15}$, —$OP(O)(OR_{18})(OR_{19})$, —$P(O)R_{20}R_{21}$, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

$R_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, in each case optionally interrupted by aryl, heteroaryl, alicyclic or heteroalicyclic;

$R_4$ is independently selected from hydrogen, or optionally substituted aliphatic, heteroaliphatic, alicyclic, heteroalicyclic, aryl, heteroaryl, alkylheteroaryl or alkylaryl;

and E is independently selected from $NR'_5$ and $NR_6$, wherein $R'_5$ is independently selected from hydrogen, optionally substituted aliphatic, heteroaliphatic, alicyclic, alkanoate, arylate, carboxyl, heteroalicyclic, aryl, heteroaryl, alkylheteroaryl or alkylaryl; or two $R_5$ species may together be selected from optionally substituted alkylene, alkenylene or alkynylene, bonded to two different N groups of the compound of structure (II);

wherein $R_6$ is independently selected from optionally substituted aliphatic, alicyclic, heteroalicyclic, aryl, heteroaryl, ether, polyether, or optionally substituted alkylaryl or alkylheteroaryl;

with the first proviso that at least one of the species E conforms to the definition given for $NR_6$;

and with the second proviso that the groups $R'_5$ and $R_6$ are not all identical with each other.

wherein $R_9$, $R_{10}$, $R_{13}$, $R_{14}$, $R_{18}$, $R_{19}$, $R_{20}$ and $R_{21}$ are independently selected from hydrogen or an optionally substituted aliphatic, heteroaliphatic, alicyclic, heteroalicyclic, aryl or heteroaryl group and $R_{15}$, $R_{16}$ and $R_{17}$ are independently selected from an optionally substituted aliphatic, heteroaliphatic, alicyclic, heteroalicyclic, aryl or heteroaryl group.

Thus these compounds of structure (Ie) are asymmetrical as regards their groups $R'_5$ and $R_6$.

In this aspect of the invention $R_1$, $R_2$, $R_3$, $R_4$, $R_5$, $R_6$, $R_9$, $R_{10}$, $R_{13}$, $R_{14}$, $R_{18}$, $R_{19}$, $R_{20}$ and $R_{21}$ may be as defined in any statement or claim contained in this specification. $R'_5$ may be as defined about for $R_5$, except that it cannot be hydrogen.

It is the process of the first aspect that enables these compounds of structure (Ie). In the process the NH group or groups in the macrocycle of structure (II) are replaced on introduction of group(s) $R_6$; whilst N-substituent group or groups already on the macrocycle (II) remain. The groups on the macrocycle, designated $R'_5$ and $R_6$ in the definition of the compounds (Ie), can be selected to be non-identical. Thus asymmetrical compounds of structure (Ie) may be provided.

Definitions

For the purpose of the present invention, an aliphatic group is a hydrocarbon moiety that may be straight chain or branched and may be completely saturated, or contain one or more units of unsaturation, but which is not aromatic. The term "unsaturated" means a moiety that has one or more double and/or triple bonds. The term "aliphatic" is therefore intended to encompass alkyl, alkenyl or alkynyl groups including multivalent equivalents such as alkylene, alkenylene and alkynylene, and combinations thereof. An aliphatic group is preferably a $C_{1-20}$ aliphatic group, that is, an aliphatic group with 1, 2, 3, 4, 5, 6, 7, 8, 9, 10, 11, 12, 13, 14, 15, 16, 17, 18, 19 or 20 carbon atoms. Preferably, an aliphatic group is a $C_{1-15}$ aliphatic, more preferably a $C_{1-12}$ aliphatic, more preferably a $C_{1-10}$ aliphatic, even more preferably a $C_{1-8}$ aliphatic, such as a $C_{1-6}$ aliphatic group.

An alkyl group is preferably a "$C_{1-20}$ alkyl group", that is an alkyl group that is a straight or branched chain with 1 to 20 carbons. The alkyl group therefore has 1, 2, 3, 4, 5, 6, 7, 8, 9, 10, 11, 12, 13, 14, 15, 16, 17, 18, 19 or 20 carbon atoms. Preferably, an alkyl group is a $C_{1-15}$ alkyl, preferably a $C_{1-12}$ alkyl, more preferably a $C_{1-10}$ alkyl, even more preferably a $C_{1-8}$ alkyl, even more preferably a $C_{1-6}$ alkyl group. Specifically, examples of "$C_{1-20}$ alkyl group" include methyl group, ethyl group, n-propyl group, iso-propyl group, n-butyl group, iso-butyl group, sec-butyl group, tert-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-ethylbutyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group and the like.

Alkenyl and alkynyl groups are preferably "$C_{2-20}$ alkenyl" and "$C_{2-20}$ alkynyl", more preferably "$C_{2-15}$ alkenyl" and "$C_{2-15}$ alkynyl", even more preferably "$C_{2-12}$ alkenyl" and "$C_{2-12}$ alkynyl", even more preferably "$C_{2-10}$ alkenyl" and "$C_{2-10}$ alkynyl", even more preferably "$C_{2-8}$ alkenyl" and "$C_{2-8}$ alkynyl", most preferably "$C_{2-6}$ alkenyl" and "$C_{2-6}$ alkynyl" groups, respectively.

Alkylene is divalent but otherwise defined as an alkyl group above. Likewise, alkenylene and alkynylene are defined as divalent equivalents of alkenyl and alkynyl above.

A heteroaliphatic group (including heteroalkyl, heteroalkenyl and heteroalkynyl) is an aliphatic group as described above, which additionally contains one or more heteroatoms. Heteroaliphatic groups therefore preferably contain from 2 to 21 atoms, preferably from 2 to 16 atoms, more preferably from 2 to 13 atoms, more preferably from 2 to 11 atoms, more preferably from 2 to 9 atoms, even more preferably from 2 to 7 atoms, wherein at least one atom is a carbon atom. Particularly preferred heteroatoms are selected from O, S, N, P and Si. When heteroaliphatic groups have two or more heteroatoms, the heteroatoms may be the same or different.

Heteroalkylene is divalent but otherwise defined as a heteroalkyl group above. Likewise, heteroalkenylene and heteroalkynylene are defined as divalent equivalents of heteroalkenyl and heteroalkynyl above. An alicyclic group is a saturated or partially unsaturated cyclic aliphatic monocyclic or polycyclic (including fused, bridging and spirofused) ring system which has from 3 to 20 carbon atoms, that is an alicyclic group with 3, 4, 5, 6, 7, 8, 9, 10, 11, 12, 13, 14, 15, 16, 17, 18, 19 or 20 carbon atoms. Preferably, an alicyclic group has from 3 to 15, more preferably from 3 to 12, even more preferably from 3 to 10, even more preferably from 3 to 8 carbon atoms, even more preferably from 3 to 6 carbons atoms. The term "alicyclic" encompasses cycloalkyl, cycloalkenyl and cycloalkynyl groups. It will be appreciated that the alicyclic group may comprise an alicyclic ring bearing one or more linking or non-linking alkyl substituents, such as —$CH_2$-cyclohexyl. Specifically, examples of the $C_{3-20}$ cycloalkyl group include cyclopropyl, cyclobutyl, cyclopentyl, cyclohexyl, cycloheptyl, adamantyl and cyclooctyl.

A heteroalicyclic group is an alicyclic group as defined above which has, in addition to carbon atoms, one or more ring heteroatoms, which are preferably selected from O, S, N, P and Si. Heteroalicyclic groups preferably contain from one to four heteroatoms, which may be the same or different. Heteroalicyclic groups preferably contain from 5 to 20 atoms, more preferably from 5 to 14 atoms, even more preferably from 5 to 12 atoms.

An aryl group is a monocyclic or polycyclic ring system having from 5 to 20 carbon atoms. An aryl group is preferably a "$C_{6-12}$ aryl group" and is an aryl group constituted by 6, 7, 8, 9, 10, 11 or 12 carbon atoms and includes condensed ring groups such as monocyclic ring group, or bicyclic ring group and the like.

Specifically, examples of "$C_{6-10}$ aryl group" include phenyl group, biphenyl group, indenyl group, naphthyl group or azulenyl group and the like. It should be noted that condensed rings such as indan and tetrahydro naphthalene are also included in the aryl group.

A heteroaryl group is an aryl group having, in addition to carbon atoms, from one to four ring heteroatoms which are preferably selected from O, S, N, P and Si. A heteroaryl group preferably has from 5 to 20, more preferably from 5 to 14 ring atoms. Specifically, examples of a heteroaryl group include pyridine, imidazole, methylimidazole and dimethylaminopyridine.

Examples of alicyclic, heteroalicyclic, aryl and heteroaryl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

Arylene is divalent but otherwise defined as an aryl group above. Likewise heteroarylene is defined as divalent equivalents of heteroaryl and cycloalkylene as divalent equivalents of alicyclic and heteroalicyclic above.

The term "halide" or "halogen" or "halo" are used interchangeably and, as used herein mean a fluorine atom, a chlorine atom, a bromine atom, an iodine atom and the like, preferably a fluorine atom, a bromine atom or a chlorine atom, and more preferably a fluorine atom.

A haloalkyl group is preferably a "$C_{1-20}$ haloalkyl group", more preferably a "$C_{1-15}$ haloalkyl group", more preferably a "$C_{1-12}$ haloalkyl group", more preferably a "$C_{1-10}$ haloalkyl group", even more preferably a "$C_{1-8}$ haloalkyl group", even more preferably a "$C_{1-6}$ haloalkyl group" and is a $C_{1-20}$ alkyl, a $C_{1-15}$ alkyl, a $C_{1-12}$ alkyl, a $C_{1-10}$ alkyl, a $C_{1-8}$ alkyl, or a $C_{1-6}$ alkyl group, respectively, as described above substituted with at least one halogen atom, preferably 1, 2 or 3 halogen atom(s). Specifically, examples of "$C_{1-20}$ haloalkyl group" include fluoromethyl group, difluoromethyl group, trifluoromethyl group, fluoroethyl group, difluroethyl group, trifluoroethyl group, chloromethyl group, bromomethyl group, iodomethyl group and the like.

An alkoxy group is preferably a "$C_{1-20}$ alkoxy group", more preferably a "$C_{1-15}$ alkoxy group", more preferably a "$C_{1-12}$ alkoxy group", more preferably a "$C_{1-10}$ alkoxy group", even more preferably a "$C_{1-8}$ alkoxy group", even more preferably a "$C_{1-6}$ alkoxy group" and is an oxy group that is bonded to the previously defined $C_{1-20}$ alkyl, $C_{1-15}$ alkyl, $C_{1-12}$ alkyl, $C_{1-10}$ alkyl, $C_{1-8}$ alkyl, or $C_{1-6}$ alkyl group respectively.

Specifically, examples of "$C_{1-20}$ alkoxy group" include methoxy group, ethoxy group, n-propoxy group, isopropoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, n-hexyloxy group, n-heptyloxy group, n-octyloxy group, n-nonyloxy group, n-decyloxy group, n-undecyloxy group, n-dodecyloxy group, n-tridecyloxy group, n-tetradecyloxy group, n-pentadecyloxy group, n-hexadecyloxy group, n-heptadecyloxy group, n-octadecyloxy group, n-nonadecyloxy group, n-eicosyloxy group, 1,1-dimethylpropoxy group, 1,2-dimethylpropoxy group, 2,2-dimethylpropoxy group, 2-methylbutoxy group, 1-ethyl-2-methylpropoxy group, 1,1,2-trimethylpropoxy group, 1,1-dimethylbutoxy group, 1,2-dimethylbutoxy group, 2,2-dimethylbutoxy group, 2,3-dimethylbutoxy group, 1,3-dimethylbutoxy group, 2-ethylbutoxy group, 2-methylpentyloxy group, 3-methylpentyloxy group and the like.

An aryloxy group is preferably a "$C_{5-20}$ aryloxy group", more preferably a "$C_{6-12}$ aryloxy group", even more preferably a "$C_{6-10}$ aryloxy group" and is an oxy group that is bonded to the previously defined $C_{5-20}$ aryl, $C_{6-12}$ aryl, or $C_{6-10}$ aryl group respectively.

An alkylthio group is preferably a "$C_{1-20}$ alkylthio group", more preferably a "$C_{1-15}$ alkylthio group", more preferably a "$C_{1-12}$ alkylthio group", more preferably a "$C_{1-10}$ alkylthio group", even more preferably a "$C_{1-8}$ alkylthio group", even more preferably a "$C_{1-6}$ alkylthio group" and is a thio (—S—) group that is bonded to the previously defined $C_{1-20}$ alkyl, $C_{1-15}$ alkyl, $C_{1-12}$ alkyl, $C_{1-10}$ alkyl, $C_{1-8}$ alkyl, or $C_{1-6}$ alkyl group respectively.

An alkylthio group utilised as a substituent as defined herein, may be connected via either a carbon atom of the alkyl group as defined above or the sulphur atom of the thio group. An arylthio group is preferably a "$C_{5-20}$ arylthio group", more preferably a "$C_{6-12}$ arylthio group", even more preferably a "$C_{6-10}$ arylthio group" and is a thio (—S—) group that is bonded to the previously defined $C_{5-20}$ aryl, $C_{6-12}$ aryl, or $C_{6-10}$ aryl group respectively.

An alkylaryl group is preferably a "$C_{6-12}$ aryl $C_{1-20}$ alkyl group", more preferably a preferably a "$C_{6-12}$ aryl $C_{1-16}$ alkyl group", even more preferably a "$C_{6-12}$ aryl $C_{1-6}$ alkyl group" and is an aryl group as defined above bonded at any position to an alkyl group as defined above. The point of attachment of the alkylaryl group to a molecule may be via the alkyl portion and thus, preferably, the alkylaryl group is —CH$_2$-Ph or —CH$_2$CH$_2$-Ph. An alkylaryl group can also be referred to as "aralkyl".

A silyl group is preferably a group —Si($R_5$)$_3$, wherein each $R_5$ can be independently an aliphatic, heteroaliphatic, alicyclic, heteroalicyclic, aryl or heteroaryl group as defined above. In certain embodiments, each $R_5$ is independently an unsubstituted aliphatic, alicyclic or aryl. Preferably, each $R_5$ is an alkyl group selected from methyl, ethyl or propyl.

A silyl ether group is preferably a group OSi($R_5$)$_3$ wherein each $R_5$ can be independently an aliphatic, heteroaliphatic, alicyclic, heteroalicyclic, aryl or heteroaryl group as defined above. In certain embodiments, each $R_5$ can be independently an unsubstituted aliphatic, alicyclic or aryl. Preferably, each $R_5$ is an optionally substituted phenyl or optionally substituted alkyl group selected from methyl, ethyl, propyl or butyl (such as n-butyl or tert-butyl (tBu)). Exemplary silyl ether groups include OSi(CH$_3$)$_3$, OSi(C$_2$H$_5$)$_3$, OSi(C$_6$H$_5$)$_3$, OSi(CH$_3$)$_2$(tBu), OSi(tBu)$_3$ and OSi(C$_6$H$_5$)$_2$(tBu).

A nitrile group (also referred to as a cyano group) is a group CN.

An imine group is a group —CR$_6$NR$_6$, preferably a group —CHNR$_6$ wherein $R_6$ is an aliphatic, heteroaliphatic, alicyclic, heteroalicyclic, aryl or heteroaryl group as defined above. In certain embodiments, $R_6$ is unsubstituted aliphatic, alicyclic or aryl. Preferably $R_6$ is an alkyl group selected from methyl, ethyl or propyl.

An acetylide group contains a triple bond —C≡C—$R_7$, preferably wherein $R_7$ can be hydrogen, an aliphatic, heteroaliphatic, alicyclic, heteroalicyclic, aryl or heteroaryl group as defined above. For the purposes of the invention when $R_7$ is alkyl, the triple bond can be present at any position along the alkyl chain. In certain embodiments, $R_7$ is unsubstituted aliphatic, alicyclic or aryl. Preferably $R_7$ is methyl, ethyl, propyl or phenyl.

An amino group is preferably —NH$_2$, —NHR$_8$ or —N($R_8$)$_2$ wherein $R_8$ can be an aliphatic, heteroaliphatic, alicyclic, heteroalicyclic, a silyl group, aryl or heteroaryl group as defined above. It will be appreciated that when the amino group is N($R_8$)$_2$, each $R_8$ group can be the same or different. In certain embodiments, each $R_8$ is independently an unsubstituted aliphatic, alicyclic, silyl or aryl. Preferably $R_8$ is methyl, ethyl, propyl, Si(CH$_3$)$_3$ or phenyl.

An amido group is preferably —NR$_9$C(O)R$_9$ or —C(O)—NR$_9$(R$_9$) wherein $R_9$ can be hydrogen, an aliphatic, heteroaliphatic, alicyclic, heteroalicyclic, aryl or heteroaryl group as defined above. In certain embodiments, $R_9$ is unsubstituted aliphatic, alicyclic or aryl. Preferably $R_9$ is hydrogen, methyl, ethyl, propyl or phenyl. The amido group may be terminated by hydrogen, an aliphatic, heteroaliphatic, alicyclic, heteroalicyclic, aryl or heteroaryl group.

An ester group is preferably —OC(O)R$_{10}$ or —C(O)OR$_{10}$ wherein $R_{10}$ can be hydrogen, an aliphatic, heteroaliphatic, alicyclic, heteroalicyclic, aryl or heteroaryl group as defined above. In certain embodiments, $R_{10}$ is unsubstituted aliphatic, alicyclic or aryl. Preferably $R_{10}$ is hydrogen, methyl, ethyl, propyl or phenyl. The ester group may be terminated by hydrogen, an aliphatic, heteroaliphatic, alicyclic, heteroalicyclic, aryl or heteroaryl group.

An ether group is preferably —OR$_{15}$ or —R$_{16}$OR$_{17}$ wherein $R_{15}$, $R_{16}$ and $R_{17}$ can be an aliphatic, heteroaliphatic, alicyclic, heteroalicyclic, aryl or heteroaryl group as defined above. In certain embodiments, $R_{15}$, $R_{16}$ and $R_{17}$ are each unsubstituted aliphatic, alicyclic or aryl. Preferably, $R_{15}$, $R_{16}$ and $R_{17}$ are each methyl, ethyl, propyl or phenyl. The ether group may be terminated by hydrogen, an aliphatic, heteroaliphatic, alicyclic, heteroalicyclic, aryl or heteroaryl group.

A sulfoxide is preferably —S(O)R$_{11}$ and a sulfonyl group is preferably —S(O)$_2$R$_{11}$ wherein $R_{11}$ can be hydrogen, an aliphatic, heteroaliphatic, alicyclic, heteroalicyclic, aryl or heteroaryl group as defined above. In certain embodiments, $R_{11}$ is unsubstituted aliphatic, alicyclic or aryl. Preferably $R_{11}$ is hydrogen, methyl, ethyl, propyl or phenyl.

A sulfinate group is preferably —OSOR$_{12}$ wherein $R_{12}$ can be hydrogen, an aliphatic, heteroaliphatic, haloaliphatic, alicyclic, heteroalicyclic, aryl or heteroaryl group as defined above. In certain embodiments, $R_{12}$ is unsubstituted aliphatic, alicyclic or aryl. Preferably $R_{12}$ is hydrogen, methyl, ethyl, propyl or phenyl.

Groups $R_{13}$, $R_{14}$, $R_{18}$, $R_{19}$, $R_{20}$ and $R_{21}$ can be a hydrogen an aliphatic, heteroaliphatic, alicyclic, heteroalicyclic, aryl or heteroaryl group as defined above. In certain embodiments, $R_{13}$, $R_{14}$, $R_{18}$, $R_{19}$, $R_{20}$ and $R_{21}$ are each unsubstituted aliphatic, alicyclic or aryl. Preferably, $R_{13}$, $R_{14}$, $R_{18}$, $R_{19}$, $R_{20}$ and $R_{21}$ are each hydrogen, methyl, ethyl, propyl or phenyl.

By the term "phosphonium" as used herein is meant the cation comprising the formula PH$_4^+$.

Any of the aliphatic (including alkyl, alkenyl, alkynyl, alkylene, alkenylene and alkynylene), heteroaliphatic, (including heteroalkyl, heteroalkenyl, heteroalkynyl, heteroalkylene, heteroalkenylene and heteroalkynylene), alicyclic, carboxylic, carboxylate, cycloalkylene, heteroalicyclic, aryl, arylene, heteroaryl, heteroarylene haloalkyl, alkoxy, aryloxy, alkylthio, arylthio, alkylaryl, silyl, silyl ether, ester, sulfoxide, sulfonyl, imine, acetylide, amino, sulfonate or amido groups wherever mentioned above, particularly when mentioned as optionally substituted above may be optionally substituted by halogen, hydroxy, nitro, alkoxy, aryloxy, alkylthio, arylthio, heteroaryloxy, alkylaryl, amino, amido, imine, nitrile, silyl, silyl ether, ester, sulfoxide, sulfonyl, acetylide, sulfonate or optionally substituted aliphatic, heteroaliphatic, alicyclic, heteroalicyclic, aryl or heteroaryl groups (for example, optionally substituted by halogen, hydroxy, nitro, alkoxy, aryloxy, alkylthio, arylthio, amino, imine, nitrile, silyl, sulfoxide, sulfonyl, sulfonate or acetylide).

When we use the term "optionally substituted" at the start of a list of chemical species we mean that all of the species in the list which can be substituted may be optionally substituted; that is we do not mean that only the first species mentioned in the list may be optionally substituted.

All of the features contained herein may be combined with any of the above aspects and in any combination.

Embodiments of the invention will now be described with reference to the following non-limiting examples.

Non-alkylated biphenol ligand precursors used in the following examples are described in WO2016/012785.

Partially alkylated biphenol ligand precursors used in the following examples were prepared using protecting group chemistry in the absence of a base, as described in WO2016/012785.

The invention will be further illustrated by means of the following non-binding examples.

EXPERIMENTAL DESCRIPTION

It should be noted here that the examples given demonstrate the breadth of applicability of the process of the present invention. The yields reported in the following examples are substantially unoptimized and reaction conditions have not been extensively tailored to suit individual target macrocycles. Some of the yields are therefore <40%, but it is understood with variation of the conditions that these yields could be substantially improved. In many cases very high yields were obtained, even without optimisation. It is noted that in each case, and as demonstrated by the enclosed NMR data, no alkylation of the phenols was observed. The products obtained were the desired tetra-N-alkylated-diphenol compounds.

Example Set 1: Preparation of Tetra-Benzylated Ligand 2

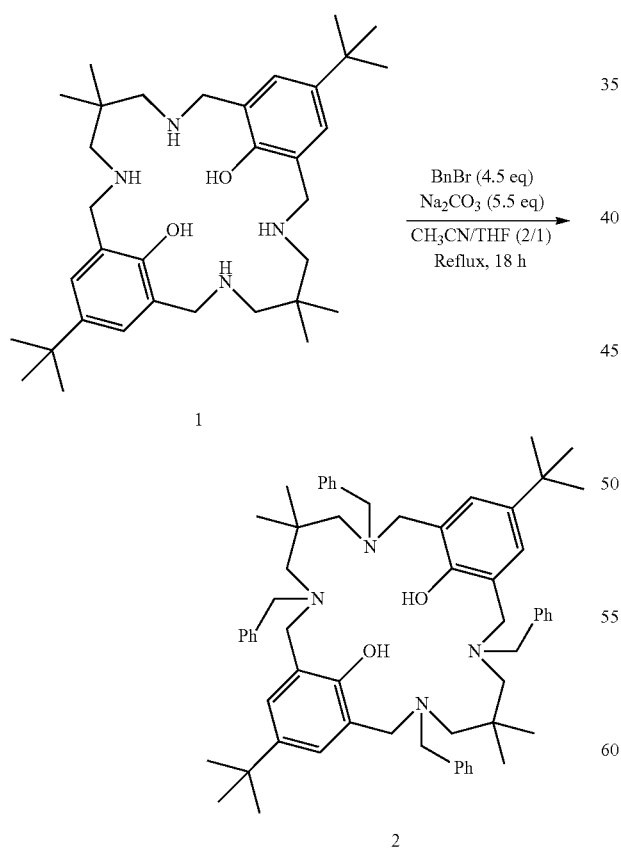

To a solution of ligand 1 (1.00 g, 1.0 eq) in tetrahydrofuran (10 mL) and acetonitrile (20 mL) were added benzyl bromide (0.96 mL, 4.5 eq) and sodium carbonate (1.05 g, 5.5 eq). The reaction mixture was stirred at reflux for 18 h. After this time, reaction mixture was filtered and the filter cake was washed with acetonitrile. The filter cake was solubilised in dichloromethane/water, and phases were separated. The aqueous phase was extracted with dichloromethane. The combined organic layers were dried over sodium sulfate, and the solvents were evaporated in vacuo to yield tetra-benzylated ligand 2 (>85%). MS (ESI): 913.6 [M+H]+; 1H NMR (400 MHz, CDCl3) δ (ppm) 10.60 (s, 2H, phenols), 7.45-7.41 (m, 8H), 7.39-7.34 (m, 8H), 7.31-7.26 (m, 4H), 6.89 (s, 4H), 3.75-3.64 (m, 16H), 2.54 (s, 8H), 1.26 (s, 18H), 0.85 (s, 12H).

Example Set 2: Preparation of Tetra-Alkylated Ligands 3, 4

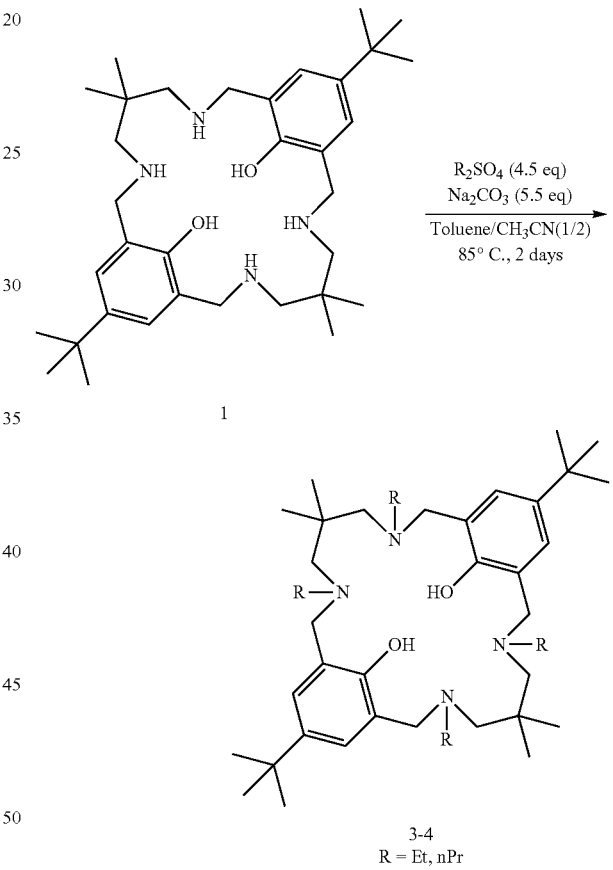

Representative procedure: To a solution of ligand 1 (1.00 g, 1.0 eq) in toluene (12 mL) and acetonitrile (24 mL) were added diethylsulfate (1.06 mL, 4.5 eq) and sodium carbonate (1.05 g, 5.5 eq). Reaction mixture was stirred at 85° C. for 2 days. After this time, reaction mixture was filtered and the mother liquor was evaporated. The residue was solubilised in dichloromethane/water, and phases were separated. The aqueous phase was extracted with dichloromethane. The combined organic layers were washed with a saturated aqueous solution of sodium hydrogen carbonate, and phases were separated. The organic layer was dried over sodium sulfate, and the solvents were evaporated in vacuo to yield tetra-alkylated ligand 3 (33%). $^1$H NMR (400 MHz, CDCl$_3$) δ (ppm) 10.68 (s, 2H, phenols), 6.95 (s, 4H), 3.63 (s, 8H), 2.55 (q, J=6.9 Hz, 8H), 2.37 (s, 8H), 1.26 (s, 18H), 1.07 (t, J=6.9 Hz, 12H), 0.78 (s, 12H). MS (ESI): 665.6 [M+H]$^+$
Mass spectrometry data for compound 4 (28%): MS (ESI): 721.6 [M+H]$^+$ Example Set 3: Preparation of Tetra-Methylated Ligands 12-19

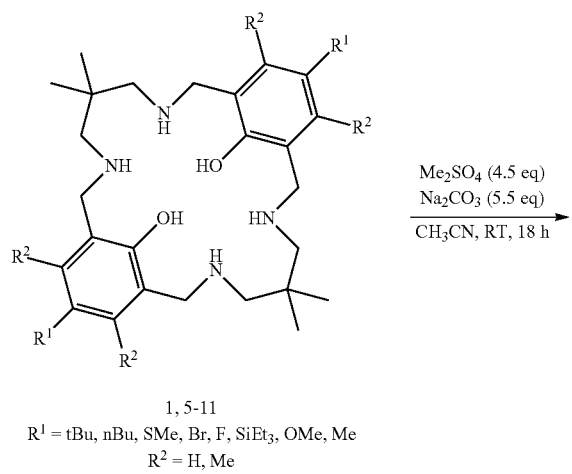

1, 5-11
R$^1$ = tBu, nBu, SMe, Br, F, SiEt$_3$, OMe, Me
R$^2$ = H, Me

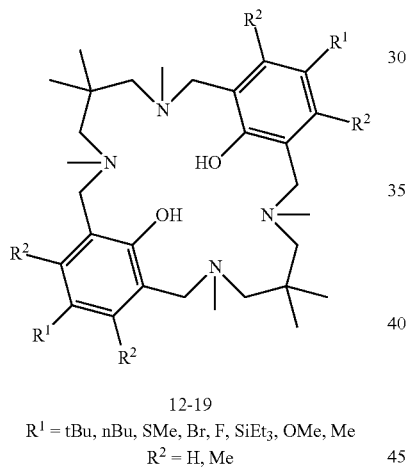

12-19
R$^1$ = tBu, nBu, SMe, Br, F, SiEt$_3$, OMe, Me
R$^2$ = H, Me

Representative procedure: To a suspension of ligand 1 (R$^1$=tBu, R$^2$=H) (1.00 g, 1.0 eq) in acetonitrile (30 mL) were added Me$_2$SO$_4$ (0.77 mL, 4.5 eq) and sodium carbonate (1.05 g, 5.5 eq). Reaction mixture was stirred at room temperature (RT) for 18 h. After this time, reaction mixture was filtered and the filter cake was washed with acetonitrile. The filter cake was solubilised in dichloromethane/water, and phases were separated. The aqueous phase was extracted with dichloromethane. The combined organic layers were dried over sodium sulfate, and the solvents were evaporated in vacuo to yield tetra-methylated ligand 12 (R$^1$=tBu, R$^2$=H>70%) as a white powder. $^1$H NMR (400 MHz, CDCl$_3$) δ (ppm) 10.99 (s, 2H, phenols), 6.96 (s, 4H), 3.59 (s, 8H), 2.38 (s, 8H), 2.33 (s, 12H), 1.29 (s, 18H), 0.89 (s, 12H). MS (ESI) 609.4 [M+H]$^+$ Mass spectrometry data for compounds 13-19:
13 (56%) (R$^1$=SMe, R$^2$=H): MS (ESI) 589.3 [M+H]$^+$
14 (53%) (R$^1$=Br, R$^2$=H): MS (ESI) 655.2 [M+H]$^+$
15 (52%) (R$^1$=F, R$^2$=H): MS (ESI) 533.4 [M+H]$^+$
16 (59%) (R$^1$=SiEt$_3$, R$^2$=H): MS (ESI) 725.5 [M+H]$^+$
17 (33%) (R$^1$=OMe, R$^2$=H): MS (ESI) 557.4 [M+H]$^+$
18 (40%) (R$^1$=nBu, R$^2$=H): MS (ESI) 609.4 [M+H]$^+$
19 (40%) (R$^1$=Me, R$^2$=Me): MS (ESI) 581.4 [M+H]$^+$ Example 4: Preparation of Tetra-Allylated Ligand 20

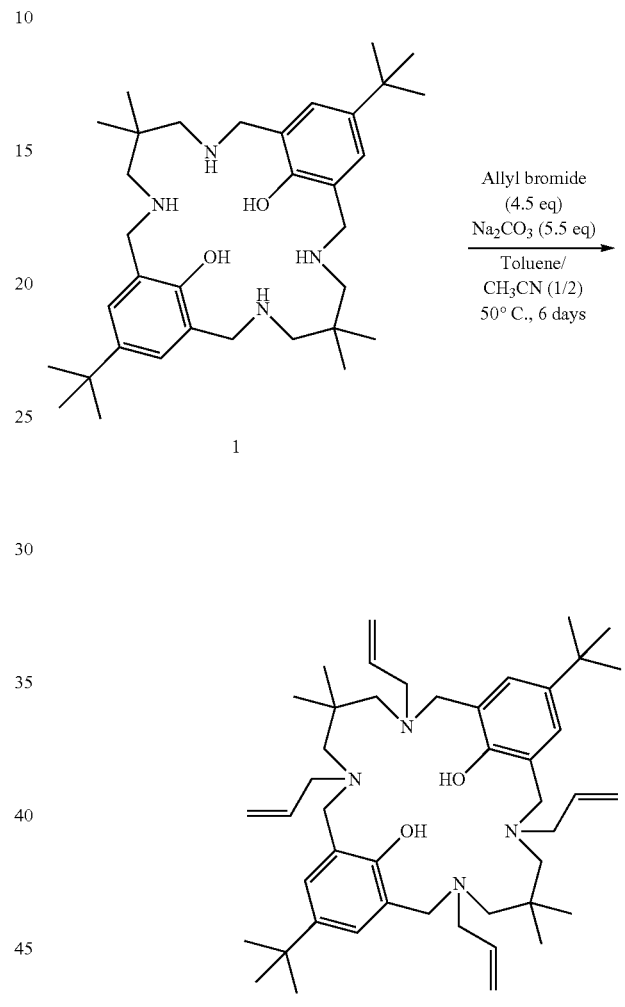

To a solution of ligand 1 (1.00 g, 1.0 eq) in toluene (10 mL) and acetonitrile (20 mL) were added allyl bromide (0.70 mL, 4.5 eq) and sodium carbonate (1.05 g, 5.5 eq). Reaction mixture was stirred at 50° C. for 6 days. After this time, reaction mixture was filtered and the filter cake was washed with acetonitrile. The filter cake was solubilised in dichloromethane/water, and phases were separated. The aqueous phase was extracted with dichloromethane. The combined organic layers were dried over sodium sulfate, and the solvents were evaporated in vacuo to yield tetra-allylated ligand 20 (>90%) as a white powder. MS (ESI) 713.6 [M+H]$^+$

Example 5: Further Preparation of Tetra-Methylated Ligand 12

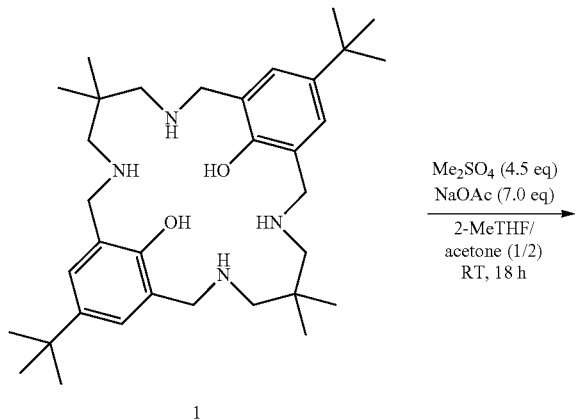

Example 6: Preparation of Tetra-Methylated Ligand 22

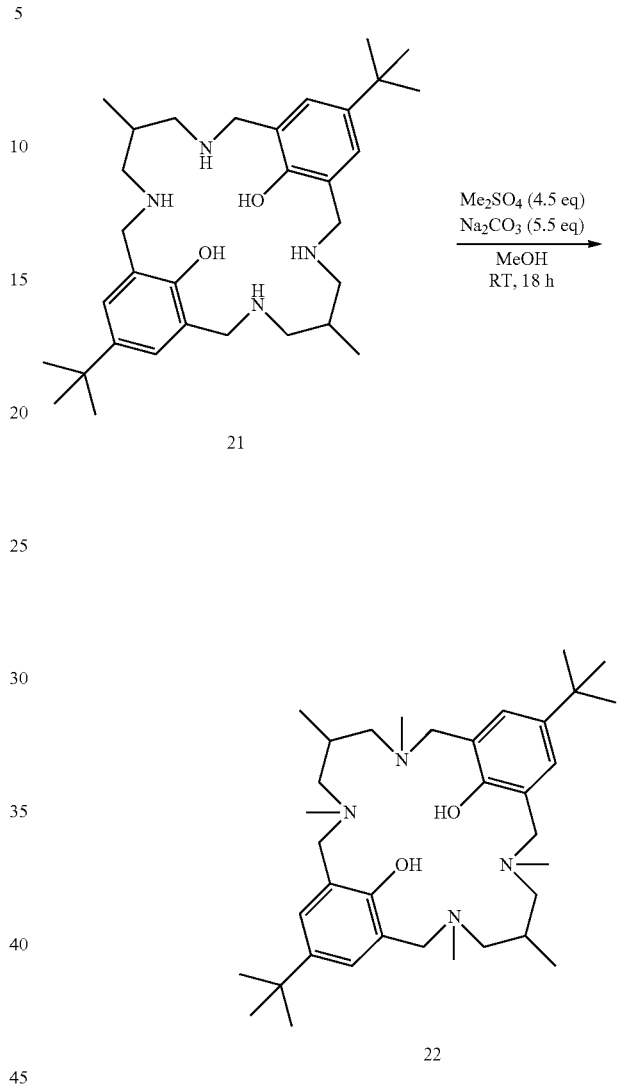

Representative example: To a solution of ligand 1 (1.00 g, 1.0 eq) in 2-methyl-tetrahydrofuran (9 mL) and acetone (18 mL) were added dimethylsulfate (0.77 mL, 4.5 eq) and sodium ethanoate (1.04 g, 7.0 eq). Reaction mixture was stirred at room temperature for 18 h. After this time, reaction mixture was filtered and the filter cake was washed with acetonitrile. The filter cake was solubilised in dichloromethane/water, and phases were separated. The aqueous phase was extracted with dichloromethane. The combined organic layers were dried over sodium sulfate, and the solvents were evaporated in vacuo to yield tetra-methylated ligand 12 (35%).

Examples of other bases used in the preparation of ligand 12:

Base=sodium hydroxide (NaOH—5.5 eq), solvent=tetrahydrofuran/acetonitrile (1:3), room temperature, 16 hours. Yield=18%.

Base=disodium phosphate ($Na_2HPO_4$— 5.5 eq), solvent=tetrahydrofuran/acetonitrile (1:3), room temperature, 16 hours. Yield=20%.

To a solution of ligand 21 (1.00 g, 1.0 eq) in methanol (30 mL) were added dimethylsulfate (0.81 mL, 4.5 eq) and sodium carbonate (1.10 g, 5.5 eq). Reaction mixture was stirred at room temperature for 18 h. After this time, reaction mixture was filtered and the mother liquor was evaporated. The residue was solubilised in dichloromethane/water, and phases were separated. The aqueous phase was extracted with dichloromethane. The combined organic layers were washed with a saturated aqueous solution of sodium hydrogen carbonate, and phases were separated. The organic layer was dried over sodium sulfate, and the solvents were evaporated. 22 (60%); MS (ESI) 581.4 [M+H]$^+$

Example 7: Preparation of Tetra-Methylated Ligand 24

Example 8: Preparation of Tri-Methylated Ligands 29-32

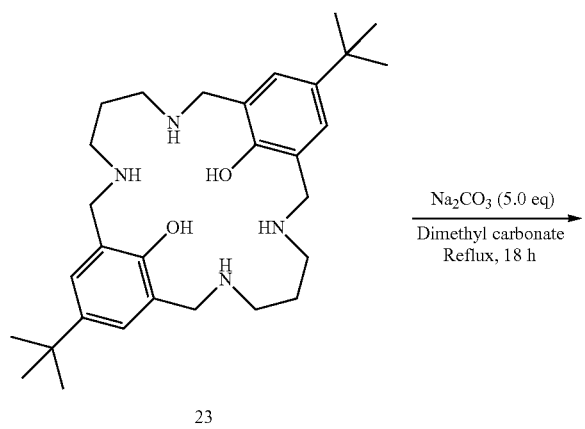

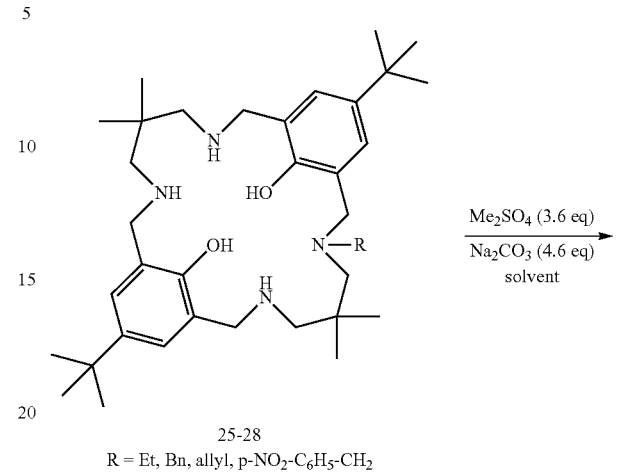

25-28
R = Et, Bn, allyl, p-NO$_2$-C$_6$H$_5$-CH$_2$

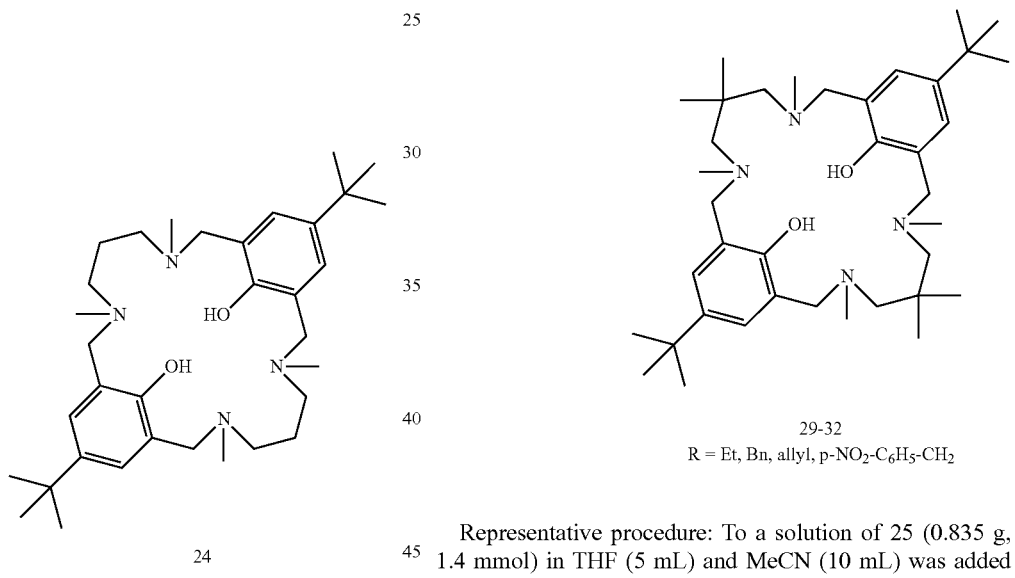

24

29-32
R = Et, Bn, allyl, p-NO$_2$-C$_6$H$_5$-CH$_2$

To a solution of ligand 23 (1.00 g, 1.0 eq) in dimethyl carbonate (30 mL) was added sodium carbonate (1.06 g, 5.0 eq). Reaction mixture was stirred at reflux for 18 h. After this time, reaction mixture was filtered and the mother liquor was evaporated. The residue was solubilised in dichloromethane/water, and phases were separated. The aqueous phase was extracted with dichloromethane. The combined organic layers were washed with a saturated aqueous solution of sodium hydrogen carbonate, and phases were separated. The organic layer was dried over sodium sulfate, and the solvents were evaporated. 24 (45%): MS (ESI) 553.4 [M+H]$^+$ Representative procedure: To a solution of 25 (0.835 g, 1.4 mmol) in THF (5 mL) and MeCN (10 mL) was added Me$_2$SO$_4$ (0.48 mL, 5.0 mmol), followed by Na$_2$CO$_3$ (0.690 g, 6.5 mmol). The reaction mixture was stirred at room temperature of 18 h. After this time, reaction mixture was filtered and the filter cake was washed with acetonitrile. The solid collected was suspended in DCM, washed with H$_2$O and saturated NaHCO$_3$, before being dried over MgSO$_4$ and reduced in volume to give 29 (70% yield) as a white solid.

$^1$H NMR (400 MHz, CDCl$_3$) δ (ppm) 10.92 (br s, 2H, phenol), 7.00 (d, 1H, J=2.5 Hz), 6.99 (d, 1H, J=2.5 Hz.), 6.85 (d, 1H, J=2.5 Hz,), 6.84 (d, 1H, J=2.5 Hz,), 3.65 (s, 2H), 3.62 (s, 2H), 3.42 (s, 2H), 3.41 (s, 2H), 2.56 (q, 4H, J=7.0 Hz), 2.40 (s, 2H), 2.37 (s, 2H), 2.33 (s, 3H), 2.33 (s, 2H), 2.31 (s, 2H), 2.25 (s, 3H), 2.23 (s, 3H), 1.25 (2xs, 18H), 1.05 (t, 3H, J=7.0 Hz), 0.86 (s, 6H), 0.83 (s, 6H). MS (ESI) m/z=623.5 [M+H]$^+$.

Data for compounds 30-32:

30 (84%) (R=Bn): MS (ESI) 685.4 [M+H]$^+$ 31 (67%) (R=allyl): MS (ESI) 635.5 [M+H]$^+$ 32 (73%) (R=p-NO$_2$—C$_6$H$_5$—CH$_2$): MS (ESI) 730.5 [M+H]$^+$

Example 9: Preparation of Tri-Ethylated and Tribenzylated Ligands 34, 35

Example 10: Preparation of Di-Ethylated and Di-Benzylated Ligands 38, 39

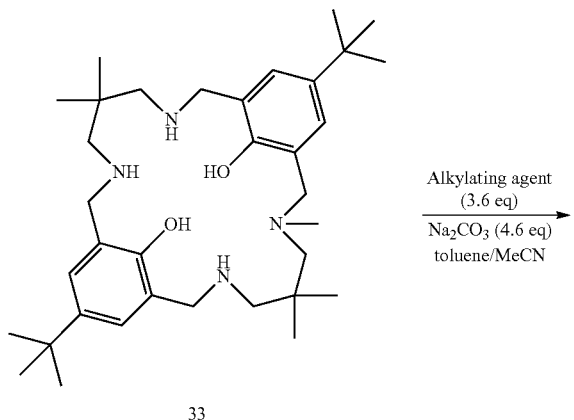

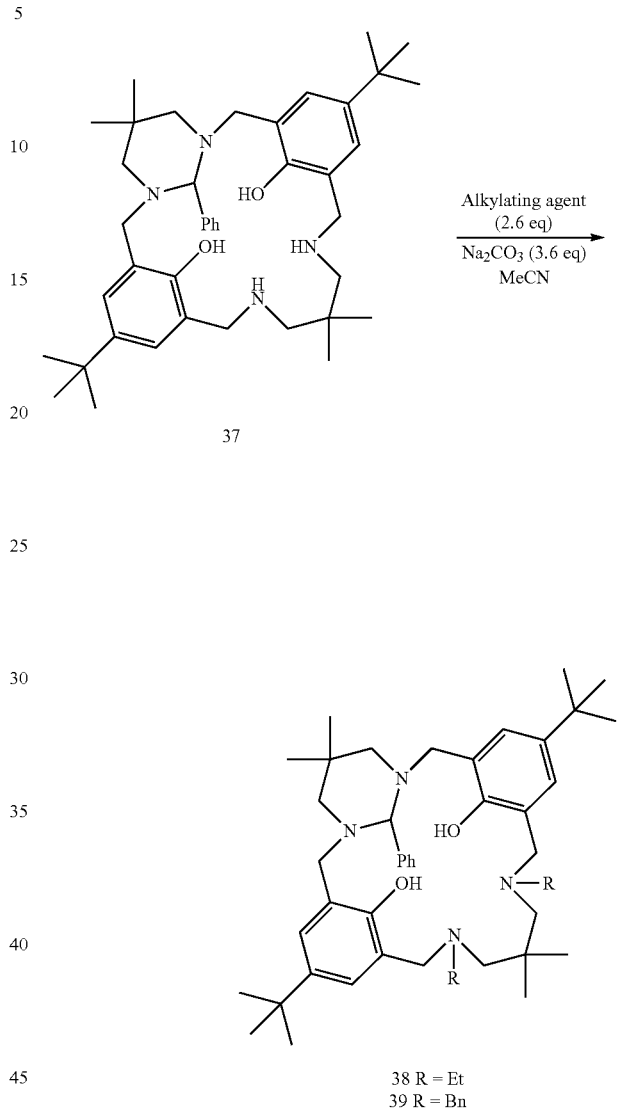

Representative example: To a solution of 33 (1.501 g, 2.6 mmol) in toluene (5 mL) and MeCN (8 mL) was added $Et_2SO_4$ (1.2 mL, 9.3 mmol), followed by $Na_2CO_3$ (1.267 g, 11.9 mmol). The reaction was stirred at 60° C. overnight. The filter cake was collected by filtration and washed with MeCN. The solid collected was suspended in DCM, washed with $H_2O$ and saturated $NaHCO_3$, before being dried over $MgSO_4$ and reduced in volume to give 34 (65% yield) as a white solid.

$^1$H NMR (400 MHz, $CDCl_3$) δ (ppm) 10.80 (br s, 2H, phenol), 6.97 (dd, 4H, J=2.5, 11.6 Hz), 6.86 (dd, 4H, J=2.4, 7.4 Hz,), 3.66 (d, 4H, J=7.8 Hz,), 3.50 (s, 2H), 3.46 (s, 2H), 2.53 (m, 6H), 2.39 (d, 4H, J=7.5 Hz.), 2.35 (s, 2H), 2.31 (s, 2H), 2.23 (3H, s), 1.25 (18H, d), 1.05 (6H, td. J=1.5, 7.0 Hz), 1.01 (t, 3H, J=7.0 Hz,), 0.82 (s, 6H), 0.79 (s, 6H). MS (ESI) 651.6 $[M+H]^+$ Data for compound 35 (74%): As per the representative example, except BnBr was used as the alkylating agent and toluene was substituted for THF. MS (ESI) 837.6 $[M+H]^+$ Representative example: 37 (2.000 g, 3 mmol), BnBr (0.93 mL, 8 mmol), and $Na_2CO_3$ (1.182 g, 11 mmol) were suspended in MeCN (30 mL) and stirred at 40° C. for 2 days. The reaction mixture was filtered, extracted into DCM, washed with $NaHCO_3$ (×3), dried over $MgSO_4$, and reduced in volume to yield 39 in 75% yield. MS (ESI) 821.6 $[M+H]^+$ Data for compound 38 (80%): As per representative example except $Et_2SO_4$ was used as the alkylating agent and the reaction was carried out in THF/MeCN (1:2). MS (ESI) 697.5 [M+H]+.

Example 11: Preparation of Cis-Dimethyl-Dialkylated Ligands 42 and 43

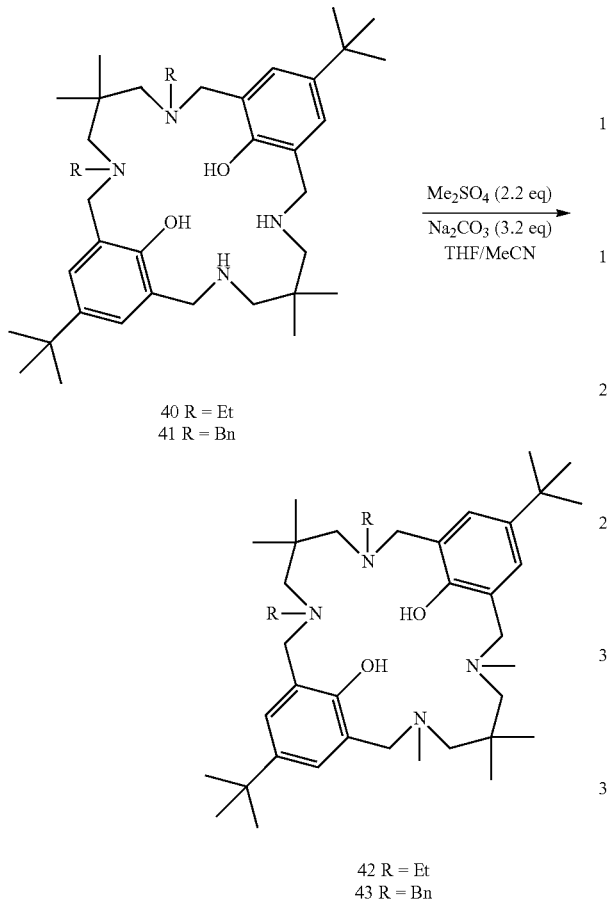

40 R = Et
41 R = Bn

42 R = Et
43 R = Bn

Representative procedure: To a solution of 40 (1 g, 1.6 mmol) in THF (3 mL) and MeCN (8 mL) was added Me$_2$SO$_4$ (0.34 mL, 3.6 mmol), followed by Na$_2$CO$_3$ (0.56 g, 5.3 mmol). The reaction mixture was stirred at room temperature overnight. After this time, the reaction mixture was filtered and the filter cake was washed with acetonitrile. The solid collected was suspended in DCM, washed with H$_2$O and saturated NaHCO$_3$, before being dried over MgSO$_4$ and reduced in volume to give 42 (72% yield) as a white solid. MS (ESI) 637.2 [M+H]$^+$.

Data for compound 43 (84%), MS (ESI) 761.2 [M+H]$^+$.

Attention is directed to all papers and document which are filed concurrently with or previous to this specification in connection with this application and which are open to the public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, expect combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract or drawings), or to any novel one, or any novel combinations, of the steps of any method or process so disclosed.

The invention claimed is:

1. A process for preparing a tetra-substituted aminobiphenol macrocyclic ligand having a structure (I), comprising the step of treating a precursor compound having a structure (II) with a compound having a structure R$_6$-L where L represents a leaving group (hereinafter compound (III)) in the presence of a base;

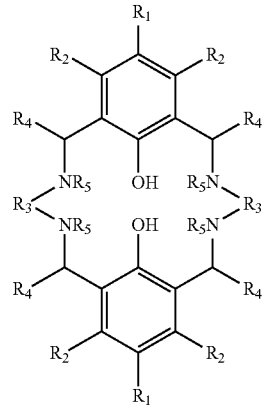

(II)

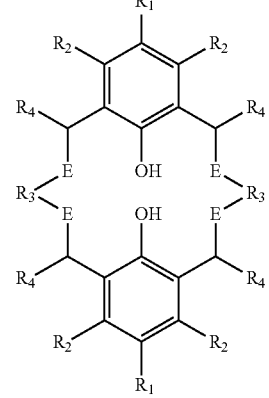

(I)

wherein R$_1$ and R$_2$ are independently selected from hydrogen, halide, a nitro group, a nitrile group, an imine group, —NCR$_{13}$R$_{14}$, an amine, an ether group —OR$_{15}$ or —R$_{16}$OR$_{17}$, an ester group —OC(O)R$_{10}$ or —C(O)OR$_{10}$, an amido group —NR$_9$C(O)R$_9$ or —C(O)—NR$_9$(R$_9$), —COOH, —C(O)R$_{15}$, —OP(O)(OR$_{18}$)(OR$_{19}$), —P(O)R$_{20}$R$_{21}$, a silyl group, a silyl ether group, a sulfoxide group, a sulfonyl group, a sulfinate group or an acetylide group or an optionally substituted alkyl, alkenyl, alkynyl, haloalkyl, aryl, heteroaryl, alkoxy, aryloxy, alkylthio, arylthio, alicyclic or heteroalicyclic group;

R$_3$ is independently selected from optionally substituted alkylene, alkenylene, alkynylene, heteroalkylene, heteroalkenylene, heteroalkynylene, arylene, heteroarylene or cycloalkylene, wherein alkylene, alkenylene, alkynylene, heteroalkylene, heteroalkenylene and heteroalkynylene, in each case optionally interrupted by aryl, heteroaryl, alicyclic or heteroalicyclic;

R$_4$ is independently selected from hydrogen, or optionally substituted aliphatic, heteroaliphatic, alicyclic, heteroalicyclic, aryl, heteroaryl, alkylheteroaryl or alkylaryl;

R$_5$ is independently selected from hydrogen, optionally substituted aliphatic, heteroaliphatic, alicyclic, alkanoate, arylate, carboxyl, heteroalicyclic, aryl, heteroaryl, alkylheteroaryl or alkylaryl, or two R5 species may together be selected from optionally substituted alkylene, alkenylene or alkynylene, bonded to two different N groups of the compound of structure (II), with the proviso that at least one of the species R$_5$ is hydrogen;

and E is independently selected from NR$_5$ and NR$_6$, with the proviso that at least one of the species E is NR$_6$;

wherein R$_6$ is independently selected from optionally substituted alkylaryl, C(2-10) alkenyl group, C(2-10) alkynyl group, C(1-10) alkyl, allyl, propargyl or benzyl;

wherein R$_9$, R$_{10}$, R$_{13}$, R$_{14}$, R$_{18}$, R$_{19}$, R$_{20}$ and R$_{21}$ are independently selected from hydrogen or an optionally substituted aliphatic, heteroaliphatic, alicyclic, heteroalicyclic, aryl or heteroaryl group and R$_{15}$, R$_{16}$ and R$_{17}$ are independently selected from an optionally substituted aliphatic, heteroaliphatic, alicyclic, heteroalicyclic, aryl or heteroaryl group; and wherein the molar ratio of compound (III) to the number of NH sites in the compound of structure (II) is at least 0.6.

2. The process of claim 1, wherein the molar ratio of the compound having the structure (III) to the number of NH sites in the macrocycle is at least 0.8.

3. The process of claim 2, wherein the molar ratio of the compound having the structure (III) to the number of NH sites in the macrocycle (II) is at least 1.

4. The process of claim 3, wherein the molar ratio of the compound having the structure (III) to the number of NH sites in the macrocycle (II) is at least 1.1.

5. The process of claim 1, wherein R$_1$ and R$_2$ are independently selected from hydrogen, halide, amino, nitro, sulfoxide, sulfonyl, sulfinate, silyl, silyl ether and an optionally substituted alkyl, alkenyl, aryl, heteroaryl, heteroalicyclic, alkoxy, aryloxy or alkylthio or arylthio.

6. The process of claim 5, wherein R$_2$ is hydrogen or alkyl and R$_1$ is independently selected from hydrogen, C$_{1-6}$alkyl, C$_{1-6}$haloalkyl, alkoxy, aryl, halide, nitro, sulfonyl, silyl or alkylthio.

7. The process of claim 6, wherein R$_2$ is hydrogen and R$_1$ is independently selected from t-butyl, n-butyl, i-propyl, methyl, piperidinyl, methoxy, hexyl methyl ether, —SCH$_3$, —S(C$_6$H$_5$), H, nitro, trimethylsilyl, triethylsilyl, methylsulfonyl (—SO$_2$CH$_3$), triethylsilyl, halogen or phenyl.

8. The process of claim 1, wherein R$_3$ is selected from alkylene, alkenylene, alkynylene, heteroalkylene, heteroalkenylene or heteroalkynylene group which may optionally be interrupted by an aryl, heteroaryl, alicyclic or heteroalicyclic group, or may be a divalent arylene or cycloalkylene group which acts as a bridging group between two nitrogen centres in the macrocycle of formula (I).

9. The process of claim 8, wherein R$_3$ is a substituted or unsubstituted alkylene, cycloalkylene, alkenylene, heteroalkylene and arylene.

10. The process of claim 9, wherein R$_3$ is selected from 2,2-dimethylpropane-1,3-diyl, ethane-1,2-diyl, 2,2-fluoropropane-1,3-diyl, 2,2- propane-1,3-diyl, butane-1,4-diyl, phenylene, cyclohexane-1,4-diyl cyclohexane-1,2-diyl or biphenylene.

11. The process of claim 1, wherein R$_4$ is independently selected from hydrogen, and optionally substituted aliphatic or aryl.

12. The process of claim 11, wherein R$_4$ is independently selected from hydrogen, and optionally substituted alkyl or aryl.

13. The process of claim 11, wherein R$_4$ groups are selected from hydrogen, methyl, ethyl, n-propyl, n-butyl, phenyl and trifluoromethyl.

14. The process of claim 1, wherein R$_5$ is independently selected from hydrogen, optionally substituted alkyl which is optionally interrupted by at least one N atom, or by at least one O atom, or by at least one S atom, optionally substituted alkylthio, alkylaryl, alkylheteroaryl, alkenyl, alkynyl, heteroalkenyl, heteroalkynyl, aryl, alicyclic, heteroalicyclic, heteroaryl, sulfonate, alkanoate (—C(O)—OR$_{10}$), arylate (arylC(O)O—), aryl-C(O)OR$_{10}$, alkylaryl-C(O)OR$_{10}$, alkyl-C(O)—OR$_{10}$, carbonyl (—C(O)—R$_{10}$), ether, polyether, alkylarylC(O)O— or carboxyl; or two R$_5$ groups together comprise an optionally substituted alkylene group bonded to two different N groups on the same macrocycle; wherein at least one species R$_5$ is hydrogen.

15. The process of claim 14, wherein R$_5$ is independently selected from optionally substituted alkyl, alkylaryl, alkenyl, alkynyl, sulfonate, alkanoate, aryl-C(O)OR$_{10}$, alkylaryl-C(O)OR$_{10}$, alkyl-C(O)—OR$_{10}$ or alkyl-C≡N.

16. The process of claim 15, wherein R$_5$ is independently selected from methyl, ethyl, propyl, butyl, allyl, propargyl, benzyl, 4-nitrobenzyl, —CH$_2$CH$_2$—C(O)—OR$_{10}$, CH$_2$CH$_2$C≡N, or —C(1-4)alkylC(O)O—, or benzoate which is unsubstituted or ring-substituted by 1, 2 or 3 C(1-4)alkyl groups.

17. The process of claim 14, wherein one species R$_5$ is hydrogen and the remaining three species R$_5$ are independently selected from the substituent group.

18. The process of claim 14 wherein two species R$_5$ are hydrogen and the remaining two species R$_5$ are independently selected from the substituent.

19. The process of claim 14, wherein three species R$_5$ are hydrogen and the remaining one species R$_5$ is independently selected from the substituent group.

20. The process of claim 14 wherein all four R$_5$ species are hydrogen.

21. The process of claim 1, wherein the compound R$_6$-L has a leaving group L which is selected from halogen, or an ether group, or a tertiary amine, or a sulfonate group of formula —O—SO$_2$—R$_x$ where R$_x$ is selected from optionally substituted aliphatic or aryl or alkylaryl; or a group of formula —O—SO$_2$—O—R$_y$ or —O—CO—O—R$_y$ where R$_y$ represents optionally substituted aliphatic or aryl or alkaryl.

22. The process of claim 21, wherein the leaving group L is a chlorine, bromine of iodine atom or a group of formula R$_y$—O—SO$_2$—O— or R$_y$—O—CO—O— where both species R$_y$ are C$_{(1-4)}$ alkyl groups or an alkyl sulfonate, aryl sulfonate, halo sulfonate or trihaloalkyl sulfonate.

23. The process of claim 1, wherein the base for use in the process is an inorganic base selected from carbonates, hydrogen carbonates, alkanoates, hydroxides, silicates, phosphates and borates of Group 1 and Group II metals, or from an organic base selected from tertiary amine bases.

24. The process of claim 23, wherein a base is selected from sodium carbonate, potassium carbonate, cesium carbonate, cesium carbonate, magnesium carbonate, calcium carbonate, ammonium carbonate, sodium hydroxide, potassium hydroxide, magnesium hydroxide, calcium hydroxide, ammonium hydroxide, sodium (C1-10) alkanoates, potassium (C1-10) alkanoates, sodium metasilicate, potassium metasilicate, sodium borate, potassium borate, trisodium phosphate, disodium phosphate, monosodium phosphate, monopotassium phosphate, dipotassium phosphate or tripotassium phosphate.

25. The process of claim 1, wherein a compound of structure (I) is prepared.

26. The process of claim 21 wherein the optionally substituted aliphatic or aryl or alkylaryl of $R_x$ includes polymer-bound sulfonate groups.

* * * * *